United States Patent
Neumann

(10) Patent No.: US 12,417,836 B2
(45) Date of Patent: Sep. 16, 2025

(54) APPARATUS AND METHOD FOR SCORING A NUTRIENT

(71) Applicant: KPN INNOVATIONS, LLC., Lakewood, CO (US)

(72) Inventor: Kenneth Neumann, Lakewood, CO (US)

(73) Assignee: KPN INNOVATIONS LLC, Lakewood, CO (US)

( * ) Notice: Subject to any disclaimer, the term of this patent is extended or adjusted under 35 U.S.C. 154(b) by 0 days.

(21) Appl. No.: 18/090,411

(22) Filed: Dec. 28, 2022

(65) Prior Publication Data

US 2024/0221901 A1 Jul. 4, 2024

(51) Int. Cl.
G16H 20/60 (2018.01)
G06F 18/2415 (2023.01)
G16H 10/60 (2018.01)

(52) U.S. Cl.
CPC ......... *G16H 20/60* (2018.01); *G06F 18/2415* (2023.01); *G16H 10/60* (2018.01)

(58) Field of Classification Search
CPC .................................................. G06F 18/2415
See application file for complete search history.

(56) References Cited

U.S. PATENT DOCUMENTS

| | | | |
|---|---|---|---|
| 9,504,408 B2 | 11/2016 | Hong et al. | |
| 9,693,724 B2 | 7/2017 | Dagum | |
| 9,824,190 B2 | 11/2017 | Sudharsan | |
| 9,852,266 B2 | 12/2017 | Damani et al. | |
| 9,892,576 B2 | 2/2018 | Kursun et al. | |
| 10,231,622 B2 | 3/2019 | Soyao et al. | |
| 10,265,028 B2 | 4/2019 | Moturu et al. | |
| 11,139,063 B1 * | 10/2021 | Neumann | G16H 10/60 |
| 11,164,669 B1 * | 11/2021 | Neumann | G16H 70/60 |
| 2007/0055551 A1 | 3/2007 | Szabo | |
| 2008/0120267 A1 | 5/2008 | Chen et al. | |
| 2008/0306770 A1 | 12/2008 | Sysko et al. | |

(Continued)

FOREIGN PATENT DOCUMENTS

| | | | | |
|---|---|---|---|---|
| WO | WO-2013123416 A2 * | 8/2013 | ........... | A61B 5/4866 |
| WO | 2019040908 | 2/2019 | | |

OTHER PUBLICATIONS

Li, D. (2022). Incorporating external knowledge into food representation and recommendation (Order No. 29254273). Available from ProQuest Dissertations and Theses Professional. (2731208512). (Year: 2022).*

(Continued)

*Primary Examiner* — Emily Huynh
(74) *Attorney, Agent, or Firm* — Caldwell Intellectual Property Law

(57) ABSTRACT

In an aspect, an apparatus for scoring a nutrient is presented. An apparatus may include at least a processor and a memory communicatively connected to the at least a processor. A memory contains instructions configuring at least a processor to receive user data from a user. At least a processor classifies a user to a profile cluster as a function of user data. At least a processor assigns the user one or more cohort labels as a function of the user data. At least a processor receives edible data. At least a processor extracts, from edible data, at least a nutrient. At least a processor scores at least a nutrient as a function of a profile cluster of a user.

18 Claims, 5 Drawing Sheets

(56) References Cited

U.S. PATENT DOCUMENTS

| | | |
|---|---|---|
| 2014/0099614 A1 | 4/2014 | Hu et al. |
| 2014/0257055 A1 | 9/2014 | Pacione et al. |
| 2015/0057634 A1 | 2/2015 | Mastrototaro et al. |
| 2016/0321413 A1 | 11/2016 | Cheyne |
| 2017/0147788 A1 | 5/2017 | Ohnemus et al. |
| 2017/0249445 A1 | 8/2017 | Devries et al. |
| 2019/0027060 A1* | 1/2019 | Ishii ....................... G06Q 30/02 |
| 2020/0321116 A1* | 10/2020 | Neumann ............... G16H 50/00 |
| 2022/0406438 A1* | 12/2022 | Gressier ............. G06Q 30/0257 |

OTHER PUBLICATIONS

Sonune, Suvarnamala; Kalbande, Dhananjay, IoT enabled API for secure transfer of medical data, Mar. 22, 2018.
Min Wu, PHD and Jake Luo, PHD, Wearable Technology Applications in Healthcare: A Literature Review, Nov. 25, 2019.

\* cited by examiner

APPARATUS AND METHOD FOR SCORING A NUTRIENT

FIELD OF THE INVENTION

The present invention generally relates to the field of nutrients and nutritional recipes. In particular, the present invention is directed to an apparatus and method for scoring a nutrient.

BACKGROUND

Many factors may need to be accounted for when preparing a meal. However, many of these factors are unoptimized across a range of phenotypes.

SUMMARY OF THE DISCLOSURE

In an aspect, an apparatus for scoring a nutrient is presented. An apparatus may include at least a processor and a memory communicatively connected to the at least a processor. A memory contains instructions configuring at least a processor to receive user data from a user. At least a processor classifies a user to a profile cluster as a function of user data. At least a processor may assign the user one or more cohort labels as a function of the user data. At least a processor receives edible data. At least a processor extracts, from edible data, at least a nutrient. At least a processor scores at least a nutrient as a function of a profile cluster of a user.

In another aspect, a method of scoring a nutrient using a computing device is presented. A method includes receiving, by a processor, user data from a user. A method includes classifying, by the processor, a user to a profile cluster as a function of user data. A method includes assigning, by the processor, the user one or more cohort labels as a function of the user data. A method includes receiving, by the processor, edible data. A method includes extracting, by the processor, from edible data, at least a nutrient. A method includes scoring, by the processor, at least a nutrient as a function of a profile cluster of a user.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to apparatuses and methods for scoring a nutrient. Aspects of the present disclosure can be used to score nutrients. Aspects of the present disclosure can also be used to provide a graphical user interface for impact factors of nutrients.

Aspects of the present disclosure allow for classification of user data to profile clusters. Exemplary embodiments illustrating aspects of the present disclosure are described below in the context of several specific examples.

Figure 1:
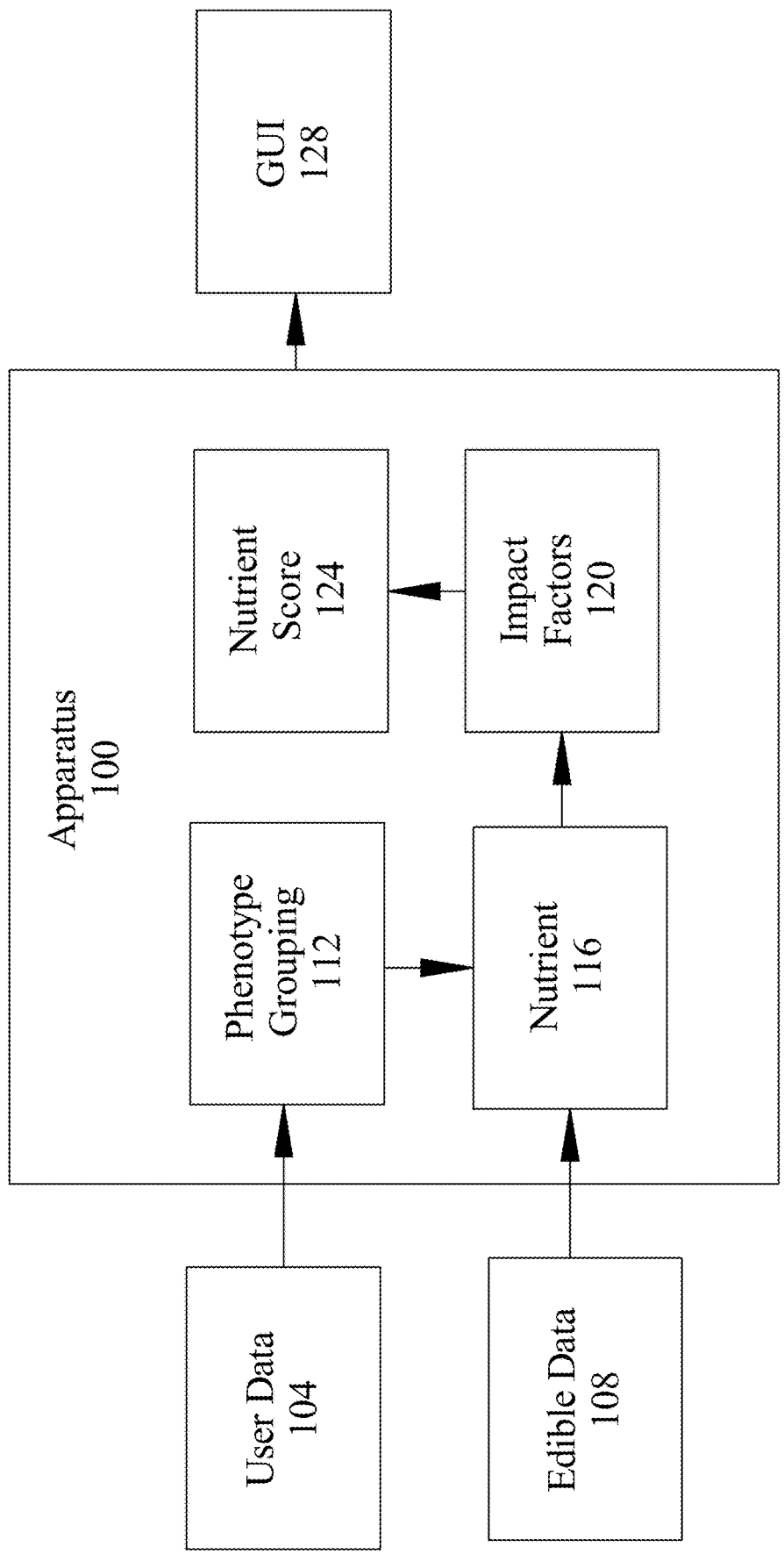
FIG. 1 is an exemplary embodiment of a block diagram of an apparatus for scoring a nutrient.

Referring now to FIG. 1, an exemplary embodiment of an apparatus 100 for generating scoring a nutrient is illustrated. Apparatus 100 may include a computing device. Apparatus 100 may include a processor and a memory communicatively connected to the processor. A memory may include instructions configuring at least a processor to perform various tasks. As used in this disclosure, "communicatively connected" means connected by way of a connection, attachment, or linkage between two or more relata which allows for reception and/or transmittance of information therebetween. For example, and without limitation, this connection may be wired or wireless, direct, or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio, and microwave data and/or signals, combinations thereof, and the like, among others. A communicative connection may be achieved, for example and without limitation, through wired or wireless electronic, digital, or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

Still referring to FIG. 1, in some embodiments, apparatus 100 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Apparatus 100 may include a single computing device operating independently, or may include two or more computing device operating in concert, in parallel, sequentially or the like; two or more computing devices may be included together in a single computing device or in two or more computing devices. Apparatus 100 may interface or communicate with one or more additional devices as described below in further detail via a network interface device. Network interface device may be utilized for connecting apparatus 100 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Apparatus 100 may include but is not limited to, for example, a computing device or cluster of computing devices in a first location and a second computing device or cluster of computing devices in a second location. Apparatus 100 may include one or more computing devices dedicated to data storage, security, distribution of traffic for load balancing, and the like. Apparatus 100 may distribute one or more computing tasks as described below across a plurality of computing devices of computing device, which may operate in parallel, in series, redundantly, or in any other manner used for distribution of tasks or memory between computing devices. Apparatus 100 may be implemented using a "shared nothing" architecture in which data is cached at the worker, in an embodiment, this may enable scalability of apparatus 100 and/or computing device.

With continued reference to FIG. 1, apparatus 100 may be designed and/or configured to perform any method, method step, or sequence of method steps in any embodiment described in this disclosure, in any order and with any degree of repetition. For instance, apparatus 100 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Apparatus 100 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, in some embodiments, apparatus 100 may be configured to receive user data 104. A "user," as used in this disclosure, is an individual. "User data" as used in this disclosure is information relating to an individual. User data 104 may include a biological extraction. A "biological extraction" as used in this disclosure includes at least an element of user physiological data. As used in this disclosure, "physiological data" is any data indicative of a person's physiological state; physiological state may be evaluated with regard to one or more measures of health of a person's body, one or more systems within a person's body such as a circulatory system, a digestive system, a nervous system, or the like, one or more organs within a person's body, and/or any other subdivision of a person's body useful for diagnostic or prognostic purposes. For instance, and without limitation, a particular set of biomarkers, test results, and/or biochemical information may be recognized in a given medical field as useful for identifying various disease conditions or prognoses within a relevant field. As a non-limiting example, and without limitation, physiological data describing red blood cells, such as red blood cell count, hemoglobin levels, hematocrit, mean corpuscular volume, mean corpuscular hemoglobin, and/or mean corpuscular hemoglobin concentration may be recognized as useful for identifying various conditions such as dehydration, high testosterone, nutrient deficiencies, kidney dysfunction, chronic inflammation, anemia, and/or blood loss. In some embodiments, user data may include physiological data.

With continued reference to FIG. 1, physiological state data may include, without limitation, hematological data, such as red blood cell count, which may include a total number of red blood cells in a person's blood and/or in a blood sample, hemoglobin levels, hematocrit representing a percentage of blood in a person and/or sample that is composed of red blood cells, mean corpuscular volume, which may be an estimate of the average red blood cell size, mean corpuscular hemoglobin, which may measure average weight of hemoglobin per red blood cell, mean corpuscular hemoglobin concentration, which may measure an average concentration of hemoglobin in red blood cells, platelet count, mean platelet volume which may measure the average size of platelets, red blood cell distribution width, which measures variation in red blood cell size, absolute neutrophils, which measures the number of neutrophil white blood cells, absolute quantities of lymphocytes such as B-cells, T-cells, Natural Killer Cells, and the like, absolute numbers of monocytes including macrophage precursors, absolute numbers of eosinophils, and/or absolute counts of basophils. Physiological state data may include, without limitation, immune function data such as Interleukine-6 (IL-6), TNF-alpha, systemic inflammatory cytokines, and the like.

Continuing to refer to FIG. 1, physiological state data may include, without limitation, data describing blood-born lipids, including total cholesterol levels, high-density lipoprotein (HDL) cholesterol levels, low-density lipoprotein (LDL) cholesterol levels, very low-density lipoprotein (VLDL) cholesterol levels, levels of triglycerides, and/or any other quantity of any blood-born lipid or lipid-containing substance. Physiological state data may include measures of glucose metabolism such as fasting glucose levels and/or hemoglobin A1-C(HbA1c) levels. Physiological state data may include, without limitation, one or more measures associated with endocrine function, such as without limitation, quantities of dehydroepiandrosterone (DHEAS), DHEA-Sulfate, quantities of cortisol, ratio of DHEAS to cortisol, quantities of testosterone quantities of estrogen, quantities of growth hormone (GH), insulin-like growth factor 1 (IGF-1), quantities of adipokines such as adiponectin, leptin, and/or ghrelin, quantities of somatostatin, progesterone, or the like. Physiological state data may include measures of estimated glomerular filtration rate (eGER). Physiological state data may include quantities of C-reactive protein, estradiol, ferritin, folate, homocysteine, prostate-specific Ag, thyroid-stimulating hormone, vitamin D, 25 hydroxy, blood urea nitrogen, creatinine, sodium, potassium, chloride, carbon dioxide, uric acid, albumin, globulin, calcium, phosphorus, alkaline phosphatase, alanine amino transferase, aspartate amino transferase, lactate dehydrogenase (LDH), bilirubin, gamma-glutamyl transferase (GGT), iron, and/or total iron binding capacity (TIBC), or the like. Physiological state data may include antinuclear antibody levels. Physiological state data may include aluminum levels. Physiological state data may include arsenic levels. Physiological state data may include levels of fibrinogen, plasma cystatin C, and/or brain natriuretic peptide.

Continuing to refer to FIG. 1, physiological state data may include measures of lung function such as forced expiratory volume, one second (FEV-1) which measures how much air can be exhaled in one second following a deep inhalation, forced vital capacity (FVC), which measures the volume of air that may be contained in the lungs. Physiological state data may include a measurement blood pressure, including without limitation systolic and diastolic blood pressure. Physiological state data may include a measure of waist circumference. Physiological state data may include body mass index (BMI). Physiological state data may include one or more measures of bone mass and/or density such as dual-energy x-ray absorptiometry. Physiological state data may include one or more measures of muscle mass. Physiological state data may include one or more measures of physical capability such as without limitation measures of grip strength, evaluations of standing balance, evaluations of gait speed, pegboard tests, timed up and go tests, and/or chair rising tests.

Still viewing FIG. 1, physiological state data may include one or more measures of cognitive function, including without limitation Rey auditory verbal learning test results, California verbal learning test results, NIH toolbox picture sequence memory test, Digital symbol coding evaluations, and/or Verbal fluency evaluations. Physiological state data may include one or more evaluations of sensory ability, including measures of audition, vision, olfaction, gustation, vestibular function and pain.

Continuing to refer to FIG. 1, physiological state data may include psychological data. Psychological data may include any data generated using psychological, neuro-psychological, and/or cognitive evaluations, as well as diagnostic screening tests, personality tests, personal compatibility tests, or the like; such data may include, without limitation, numerical score data entered by an evaluating professional and/or by a subject performing a self-test such as a computerized questionnaire. Psychological data may include textual, video, or image data describing testing, analysis, and/or conclusions entered by a medical professional such as without limitation a psychologist, psychiatrist, psychotherapist, social worker, a medical doctor, or the like. Psychological data may include data gathered from user interactions with persons, documents, and/or computing devices 104; for instance, user patterns of purchases, including electronic purchases, communication such as via chat-rooms or the like, any textual, image, video, and/or data produced by the subject, any textual image, video and/or other data depicting and/or describing the subject, or the like. Any psychological data and/or data used to generate psychological data may be analyzed using machine-learning and/or language processing module as described in this disclosure.

Still referring to FIG. 1, physiological state data may include genomic data, including deoxyribonucleic acid (DNA) samples and/or sequences, such as without limitation DNA sequences contained in one or more chromosomes in human cells. Genomic data may include, without limitation, ribonucleic acid (RNA) samples and/or sequences, such as samples and/or sequences of messenger RNA (mRNA) or the like taken from human cells. Genetic data may include telomere lengths. Genomic data may include epigenetic data including data describing one or more states of methylation of genetic material. Physiological state data may include proteomic data, which as used herein is data describing all proteins produced and/or modified by an organism, colony of organisms, or system of organisms, and/or a subset thereof. Physiological state data may include data concerning a microbiome of a person, which as used herein includes any data describing any microorganism and/or combination of microorganisms living on or within a person, including without limitation biomarkers, genomic data, proteomic data, and/or any other metabolic or biochemical data useful for analysis of the effect of such microorganisms on other physiological state data of a person, as described in further detail below.

With continuing reference to FIG. 1, physiological state data may include one or more user-entered descriptions of a person's physiological state. One or more user-entered descriptions may include, without limitation, user descriptions of symptoms, which may include without limitation current or past physical, psychological, perceptual, and/or neurological symptoms, user descriptions of current or past physical, emotional, and/or psychological problems and/or concerns, user descriptions of past or current treatments, including therapies, nutritional regimens, exercise regimens, pharmaceuticals or the like, or any other user-entered data that a user may provide to a medical professional when seeking treatment and/or evaluation, and/or in response to medical intake papers, questionnaires, questions from medical professionals, or the like. Physiological state data may include any physiological state data, as described above, describing any multicellular organism living in or on a person including any parasitic and/or symbiotic organisms living in or on the persons; non-limiting examples may include mites, nematodes, flatworms, or the like. Examples of physiological state data described in this disclosure are presented for illustrative purposes only and are not meant to be exhaustive.

With continued reference to FIG. 1, physiological data may include, without limitation any result of any medical test, physiological assessment, cognitive assessment, psychological assessment, or the like. Apparatus 100 may receive at least a physiological data from one or more other devices after performance; apparatus 100 may alternatively or additionally perform one or more assessments and/or tests to obtain at least a physiological data, and/or one or more portions thereof, on apparatus 100. For instance, at least physiological data may include or more entries by a user in a form or similar graphical user interface object; one or more entries may include, without limitation, user responses to questions on a psychological, behavioral, personality, or cognitive test. For instance, at least a server may present to user a set of assessment questions designed or intended to evaluate a current state of mind of the user, a current psychological state of the user, a personality trait of the user, or the like; at least a server may provide user-entered responses to such questions directly as at least a physiological data and/or may perform one or more calculations or other algorithms to derive a score or other result of an assessment as specified by one or more testing protocols, such as automated calculation of a Stanford-Binet and/or Wechsler scale for IQ testing, a personality test scoring such as a Myers-Briggs test protocol, or other assessments that may occur to persons skilled in the art upon reviewing the entirety of this disclosure.

With continued reference to FIG. 1, assessment and/or self-assessment data, and/or automated or other assessment results, obtained from a third-party device; third-party device may include, without limitation, a server or other device (not shown) that performs automated cognitive, psychological, behavioral, personality, or other assessments. Third-party device may include a device operated by an informed advisor. An informed advisor may include any medical professional who may assist and/or participate in the medical treatment of a user. An informed advisor may include a medical doctor, nurse, physician assistant, pharmacist, yoga instructor, nutritionist, spiritual healer, meditation teacher, fitness coach, health coach, life coach, and the like.

With continued reference to FIG. 1, physiological data may include data describing one or more test results, including results of mobility tests, stress tests, dexterity tests, endocrinal tests, genetic tests, and/or electromyographic tests, biopsies, radiological tests, genetic tests, and/or sensory tests. Persons skilled in the art, upon reviewing the entirety of this disclosure, will be aware of various additional examples of at least a physiological sample consistent with this disclosure.

With continued reference to FIG. 1, physiological data may include one or more user body measurements. A "user body measurement" as used in this disclosure, includes a measurable indicator of the severity, absence, and/or presence of a disease state. A "disease state" as used in this disclosure, includes any harmful deviation from the normal structural and/or function state of a human being. A disease state may include any medical condition and may be associated with specific symptoms and signs. A disease state may be classified into different types including infectious diseases, deficiency diseases, hereditary diseases, and/or physiological diseases. For instance and without limitation, internal dysfunction of the immune system may produce a variety of different diseases including immunodeficiency, hypersensitivity, allergies, and/or autoimmune disorders.

With continued reference to FIG. 1, user body measurements may be related to particular dimensions of the human body. A "dimension of the human body" as used in this disclosure, includes one or more functional body systems that are impaired by disease in a human body and/or animal body. Functional body systems may include one or more body systems recognized as attributing to root causes of disease by functional medicine practitioners and experts. A "root cause" as used in this disclosure, includes any chain of causation describing underlying reasons for a particular disease state and/or medical condition instead of focusing solely on symptomatology reversal. Root cause may include chains of causation developed by functional medicine practices that may focus on disease causation and reversal. For instance and without limitation, a medical condition such as diabetes may include a chain of causation that does not include solely impaired sugar metabolism but that also includes impaired hormone systems including insulin resistance, high cortisol, less than optimal thyroid production, and low sex hormones. Diabetes may include further chains of causation that include inflammation, poor diet, delayed food allergies, leaky gut, oxidative stress, damage to cell membranes, and dysbiosis. Dimensions of the human body may include but are not limited to epigenetics, gut-wall, microbiome, nutrients, genetics, and/or metabolism.

With continued reference to FIG. 1, epigenetic, as used herein, includes any user body measurements describing changes to a genome that do not involve corresponding changes in nucleotide sequence. Epigenetic body measurement may include data describing any heritable phenotypic. Phenotype, as used herein, may include any observable trait of a user including morphology, physical form, and structure. Phenotype may include a user's biochemical and physiological properties, behavior, and products of behavior. Behavioral phenotypes may include cognitive, personality, and behavior patterns. This may include effects on cellular and physiological phenotypic traits that may occur due to external or environmental factors. For example, DNA methylation and histone modification may alter phenotypic expression of genes without altering underlying DNA sequence. Epigenetic body measurements may include data describing one or more states of methylation of genetic material.

With continued reference to FIG. 1, gut-wall, as used herein, includes the space surrounding the lumen of the gastrointestinal tract that is composed of four layers including the mucosa, submucosa, muscular layer, and serosa. The mucosa contains the gut epithelium that is composed of goblet cells that function to secrete mucus, which aids in lubricating the passage of food throughout the digestive tract. The goblet cells also aid in protecting the intestinal wall from destruction by digestive enzymes. The mucosa includes villi or folds of the mucosa located in the small intestine that increase the surface area of the intestine. The villi contain a lacteal, that is a vessel connected to the lymph system that aids in removal of lipids and tissue fluids. Villi may contain microvilli that increase the surface area over which absorption can take place. The large intestine lack villi and instead a flat surface containing goblet cells are present.

With continued reference to FIG. 1, gut-wall includes the submucosa, which contains nerves, blood vessels, and elastic fibers containing collagen. Elastic fibers contained within the submucosa aid in stretching the gastrointestinal tract with increased capacity while also maintaining the shape of the intestine. Gut-wall includes muscular layer which contains smooth muscle that aids in peristalsis and the movement of digested material out of and along the gut. Gut-wall includes the serosa which is composed of connective tissue and coated in mucus to prevent friction damage from the intestine rubbing against other tissue. Mesenteries are also found in the serosa and suspend the intestine in the abdominal cavity to stop it from being disturbed when a person is physically active.

With continued reference to FIG. 1, gut-wall body measurement may include data describing one or more test results including results of gut-wall function, gut-wall integrity, gut-wall strength, gut-wall absorption, gut-wall permeability, intestinal absorption, gut-wall barrier function, gut-wall absorption of bacteria, gut-wall malabsorption, gut-wall gastrointestinal imbalances and the like.

With continued reference to FIG. 1, gut-wall body measurement may include any data describing blood test results of creatinine levels, lactulose levels, zonulin levels, and mannitol levels. Gut-wall body measurement may include blood test results of specific gut-wall body measurements including d-lactate, endotoxin lipopolysaccharide (LPS) Gut-wall body measurement may include data breath tests measuring lactulose, hydrogen, methane, lactose, and the like. Gut-wall body measurement may include blood test results describing blood chemistry levels of albumin, bilirubin, complete blood count, electrolytes, minerals, sodium, potassium, calcium, glucose, blood clotting factors, With continued reference to FIG. 1, gut-wall body measurement may include one or more stool test results describing presence or absence of parasites, firmicutes, Bacteroidetes, absorption, inflammation, food sensitivities. Stool test results may describe presence, absence, and/or measurement of acetate, aerobic bacterial cultures, anerobic bacterial cultures, fecal short chain fatty acids, beta-glucuronidase, cholesterol, chymotrypsin, fecal color, *Cryptosporidium* EIA, *Entamoeba histolytica*, fecal lactoferrin, *Giardia lamblia* EIA, long chain fatty acids, meat fibers and vegetable fibers, mucus, occult blood, parasite identification, phospholipids, propionate, putrefactive short chain fatty acids, total fecal fat, triglycerides, yeast culture, n-butyrate, pH and the like.

With continued reference to FIG. 1, gut-wall body measurement may include one or more stool test results describing presence, absence, and/or measurement of microorganisms including bacteria, archaea, fungi, protozoa, algae, viruses, parasites, worms, and the like. Stool test results may contain species such as *Bifidobacterium* species, *campylobacter* species, *Clostridium difficile*, *cryptosporidium* species, *Cyclospora cayetanensis*, *Cryptosporidium* EIA, *Dientamoeba fragilis*, *Entamoeba histolytica*, *Escherichia coli*, *Entamoeba histolytica*, *Giardia*, *H. pylori*, *Candida albicans*, *Lactobacillus* species, worms, macroscopic worms, mycology, protozoa, Shiga toxin *E. coli*, and the like.

With continued reference to FIG. 1, gut-wall body measurement may include one or more microscopic ova exam results, microscopic parasite exam results, protozoan polymerase chain reaction test results and the like. Gut-wall body measurement may include enzyme-linked immunosorbent assay (ELISA) test results describing immunoglobulin G (Ig G) food antibody results, immunoglobulin E (Ig E) food antibody results, Ig E mold results, IgG spice and herb results. Gut-wall body measurement may include measurements of calprotectin, eosinophil protein x (EPX), stool weight, pancreatic elastase, total urine volume, blood creatinine levels, blood lactulose levels, blood mannitol levels.

With continued reference to FIG. 1, gut-wall body measurement may include one or more elements of data describing one or more procedures examining gut including for example colonoscopy, endoscopy, large and small molecule challenge and subsequent urinary recovery using large molecules such as lactulose, polyethylene glycol-3350, and small molecules such as mannitol, L-rhamnose, polyethyleneglycol-300. Gut-wall body measurement may include data describing one or more images such as x-ray, MRI, CT scan, ultrasound, standard barium follow-through examination, barium enema, barium with contract, MRI fluoroscopy, positron emission tomography 9PET), diffusion-weighted MRI imaging, and the like.

With continued reference to FIG. 1, microbiome, as used herein, includes ecological community of commensal, symbiotic, and pathogenic microorganisms that reside on or within any of a number of human tissues and biofluids. For example, human tissues and biofluids may include the skin, mammary glands, placenta, seminal fluid, uterus, vagina, ovarian follicles, lung, saliva, oral mucosa, conjunctiva, biliary, and gastrointestinal tracts. Microbiome may include for example, bacteria, archaea, protists, fungi, and viruses. Microbiome may include commensal organisms that exist within a human being without causing harm or disease. Microbiome may include organisms that are not harmful but rather harm the human when they produce toxic metabolites such as trimethylamine. Microbiome may include pathogenic organisms that cause host damage through virulence factors such as producing toxic by-products. Microbiome may include populations of microbes such as bacteria and yeasts that may inhabit the skin and mucosal surfaces in various parts of the body. Bacteria may include for example Firmicutes species, Bacteroidetes species, Proteobacteria species, Verrumicrobia species, Actinobacteria species, Fusobacteria species, Cyanobacteria species and the like. Archaea may include methanogens such as Methanobrevibacter smithies' and Methanosphaera stadtmanae. Fungi may include *Candida* species and *Malassezia* species. Viruses may include bacteriophages. Microbiome species may vary in different locations throughout the body. For example, the genitourinary system may contain a high prevalence of *Lactobacillus* species while the gastrointestinal tract may contain a high prevalence of *Bifidobacterium* species while the lung may contain a high prevalence of *Streptococcus* and *Staphylococcus* species.

With continued reference to FIG. 1, microbiome body measurement may include one or more stool test results describing presence, absence, and/or measurement of microorganisms including bacteria, archaea, fungi, protozoa, algae, viruses, parasites, worms, and the like. Stool test results may contain species such as Ackerman's muciniphila, Anaerotruncus colihominis, bacteriology, *Bacteroides* vulgates', *Bacteroides-Prevotella*, *Barnesiella* species, *Bifidobacterium* longarm, *Bifidobacterium* species, *Butyrivbrio crossotus*, *Clostridium* species, *Collinsella aerofaciens*, fecal color, fecal consistency, *Coprococcus eutactus*, *Desulfovibrio piger*, *Escherichia coli*, *Faecalibacterium prausnitzii*, Fecal occult blood, Firmicutes to Bacteroidetes ratio, *Fusobacterium* species, *Lactobacillus* species, Methanobrevibacter *smithii*, yeast minimum inhibitory concentration, bacteria minimum inhibitory concentration, yeast mycology, fungi mycology, Odoribacter species, *Oxalobacter formigenes*, parasitology, *Prevotella* species, *Pseudoflavonifractor* species, *Roseburia* species, *Ruminococcus* species, *Veillonella* species and the like.

With continued reference to FIG. 1, microbiome body measurement may include one or more stool tests results that identify all microorganisms living a user's gut including bacteria, viruses, archaea, yeast, fungi, parasites, and bacteriophages. Microbiome body measurement may include DNA and RNA sequences from live microorganisms that may impact a user's health. Microbiome body measurement may include high resolution of both species and strains of all microorganisms. Microbiome body measurement may include data describing current microbe activity. Microbiome body measurement may include expression of levels of active microbial gene functions. Microbiome body measurement may include descriptions of sources of disease-causing microorganisms, such as viruses found in the gastrointestinal tract such as raspberry bushy swarf virus from consuming contaminated raspberries or Pepino mosaic virus from consuming contaminated tomatoes.

With continued reference to FIG. 1, microbiome body measurement may include one or more blood test results that identify metabolites produced by microorganisms. Metabolites may include for example, indole-3-propionic acid, indole-3-lactic acid, indole-3-acetic acid, tryptophan, serotonin, kynurenine, total indoxyl sulfate, tyrosine, xanthine, 3-methylxanthine, uric acid, and the like.

With continued reference to FIG. 1, microbiome body measurement may include one or more breath test results that identify certain strains of microorganisms that may be present in certain areas of a user's body. This may include for example, lactose intolerance breath tests, methane-based breath tests, hydrogen-based breath tests, fructose-based breath tests, *Helicobacter pylori* breath test, fructose intolerance breath test, bacterial overgrowth syndrome breath tests and the like.

With continued reference to FIG. 1, microbiome body measurement may include one or more urinary analysis results for certain microbial strains present in urine. This may include for example, urinalysis that examines urine specific gravity, urine cytology, urine sodium, urine culture, urinary calcium, urinary hematuria, urinary glucose levels, urinary acidity, urinary protein, urinary nitrites, bilirubin, red blood cell urinalysis, and the like.

With continued reference to FIG. 1, nutrient as used herein, includes any substance required by the human body to function. Nutrients may include carbohydrates, protein, lipids, vitamins, minerals, antioxidants, fatty acids, amino acids, and the like. Nutrients may include for example vitamins such as thiamine, riboflavin, niacin, pantothenic acid, pyridoxine, biotin, folate, cobalamin, Vitamin C, Vitamin A, Vitamin D, Vitamin E, and Vitamin K. Nutrients may include for example minerals such as sodium, chloride, potassium, calcium, phosphorous, magnesium, sulfur, iron, zinc, iodine, selenium, copper, manganese, fluoride, chromium, molybdenum, nickel, aluminum, silicon, vanadium, arsenic, and boron.

With continued reference to FIG. 1, nutrients may include extracellular nutrients that are free floating in blood and exist outside of cells. Extracellular nutrients may be located in serum. Nutrients may include intracellular nutrients which may be absorbed by cells including white blood cells and red blood cells.

With continued reference to FIG. 1, nutrient body measurement may include one or more blood test results that identify extracellular and intracellular levels of nutrients. Nutrient body measurement may include blood test results that identify serum, white blood cell, and red blood cell levels of nutrients. For example, nutrient body measurement may include serum, white blood cell, and red blood cell levels of micronutrients such as Vitamin A, Vitamin B1, Vitamin B2, Vitamin B3, Vitamin B6, Vitamin B12, Vitamin B5, Vitamin C, Vitamin D, Vitamin E, Vitamin K1, Vitamin K2, and folate.

With continued reference to FIG. 1, nutrient body measurement may include one or more blood test results that identify serum, white blood cell and red blood cell levels of nutrients such as calcium, manganese, zinc, copper, chromium, iron, magnesium, copper to zinc ratio, choline, inositol, carnitine, methylmalonic acid (MMA), sodium, potassium, asparagine, glutamine, serine, coenzyme q10, cysteine, alpha lipoic acid, glutathione, selenium, eicosapentaenoic acid (EPA), docosahexaenoic acid (DHA), docosapentaenoic acid (DPA), total omega-3, lauric acid, arachidonic acid, oleic acid, total omega 6, and omega 3 index.

With continued reference to FIG. 1, nutrient body measurement may include one or more salivary test results that identify levels of nutrients including any of the nutrients as described herein. Nutrient body measurement may include hair analysis of levels of nutrients including any of the nutrients as described herein.

With continued reference to FIG. 1, genetic as used herein, includes any inherited trait. Inherited traits may include genetic material contained with DNA including for example, nucleotides. Nucleotides include adenine (A), cytosine (C), guanine (G), and thymine (T). Genetic information may be contained within the specific sequence of an individual's nucleotides and sequence throughout a gene or DNA chain. Genetics may include how a particular genetic sequence may contribute to a tendency to develop a certain disease such as cancer or Alzheimer's disease.

With continued reference to FIG. 1, genetic body measurement may include one or more results from one or more blood tests, hair tests, skin tests, urine, amniotic fluid, buccal swabs and/or tissue test to identify a user's particular sequence of nucleotides, genes, chromosomes, and/or proteins. Genetic body measurement may include tests that example genetic changes that may lead to genetic disorders. Genetic body measurement may detect genetic changes such as deletion of genetic material or pieces of chromosomes that may cause Duchenne Muscular Dystrophy. Genetic body measurement may detect genetic changes such as insertion of genetic material into DNA or a gene such as the BRCA1 gene that is associated with an increased risk of breast and ovarian cancer due to insertion of 2 extra nucleotides. Genetic body measurement may include a genetic change such as a genetic substitution from a piece of genetic material that replaces another as seen with sickle cell anemia where one nucleotide is substituted for another. Genetic body measurement may detect a genetic change such as a duplication when extra genetic material is duplicated one or more times within a person's genome such as with Charcot-Marie Tooth disease type 1. Genetic body measurement may include a genetic change such as an amplification when there is more than a normal number of copies of a gene in a cell such as HER2 amplification in cancer cells. Genetic body measurement may include a genetic change such as a chromosomal translocation when pieces of chromosomes break off and reattach to another chromosome such as with the BCR-ABL1 gene sequence that is formed when pieces of chromosome 9 and chromosome 22 break off and switch places. Genetic body measurement may include a genetic change such as an inversion when one chromosome experiences two breaks and the middle piece is flipped or inverted before reattaching. Genetic body measurement may include a repeat such as when regions of DNA contain a sequence of nucleotides that repeat a number of times such as for example in Huntington's disease or Fragile X syndrome. Genetic body measurement may include a genetic change such as a trisomy when there are three chromosomes instead of the usual pair as seen with Down syndrome with a trisomy of chromosome 21, Edwards syndrome with a trisomy at chromosome 18 or Patau syndrome with a trisomy at chromosome 13. Genetic body measurement may include a genetic change such as monosomy such as when there is an absence of a chromosome instead of a pair, such as in Turner syndrome.

With continued reference to FIG. 1, genetic body measurement may include an analysis of COMT gene that is responsible for producing enzymes that metabolize neurotransmitters. Genetic body measurement may include an analysis of DRD2 gene that produces dopamine receptors in the brain. Genetic body measurement may include an analysis of ADRA2B gene that produces receptors for noradrenaline. Genetic body measurement may include an analysis of 5-HTTLPR gene that produces receptors for serotonin. Genetic body measurement may include an analysis of BDNF gene that produces brain derived neurotrophic factor. Genetic body measurement may include an analysis of 9p21 gene that is associated with cardiovascular disease risk. Genetic body measurement may include an analysis of APOE gene that is involved in the transportation of blood lipids such as cholesterol. Genetic body measurement may include an analysis of NOS3 gene that is involved in producing enzymes involved in regulating vasodilation and vasoconstriction of blood vessels.

With continued reference to FIG. 1, genetic body measurement may include ACE gene that is involved in producing enzymes that regulate blood pressure. Genetic body measurement may include SLCO1B1 gene that directs pharmaceutical compounds such as statins into cells. Genetic body measurement may include FUT2 gene that produces enzymes that aid in absorption of Vitamin B12 from digestive tract. Genetic body measurement may include MTHFR gene that is responsible for producing enzymes that aid in metabolism and utilization of Vitamin B9 or folate. Genetic body measurement may include SHMT1 gene that aids in production and utilization of Vitamin B9 or folate. Genetic body measurement may include MTRR gene that produces enzymes that aid in metabolism and utilization of Vitamin B12. Genetic body measurement may include MTR gene that produces enzymes that aid in metabolism and utilization of Vitamin B12. Genetic body measurement may include FTO gene that aids in feelings of satiety or fulness after eating. Genetic body measurement may include MC4R gene that aids in producing hunger cues and hunger triggers. Genetic body measurement may include APOA2 gene that directs body to produce ApoA2 thereby affecting absorption of saturated fats. Genetic body measurement may include UCP1 gene that aids in controlling metabolic rate and thermoregulation of body. Genetic body measurement may include TCF7L2 gene that regulates insulin secretion. Genetic body measurement may include AMY1 gene that aids in digestion of starchy foods. Genetic body measurement may include MCM6 gene that controls production of lactase enzyme that aids in digesting lactose found in dairy products. Genetic body measurement may include BCMO1 gene that aids in producing enzymes that aid in metabolism and activation of Vitamin A. Genetic body measurement may include SLC23A1 gene that produce and transport Vitamin C. Genetic body measurement may include CYP2R1 gene that produce enzymes involved in production and activation of Vitamin D. Genetic body measurement may include GC gene that produce and transport Vitamin D. Genetic body measurement may include CYP1A2 gene that aid in metabolism and elimination of caffeine. Genetic body measurement may include CYP17A1 gene that produce enzymes that convert progesterone into androgens such as androstenedione, androstendiol, dehydroepiandrosterone, and testosterone.

With continued reference to FIG. 1, genetic body measurement may include CYP19A1 gene that produce enzymes that convert androgens such as androstenedione and testosterone into estrogens including estradiol and estrone. Genetic body measurement may include SRD5A2 gene that aids in production of enzymes that convert testosterone into dihydrotestosterone. Genetic body measurement may include UFT2B17 gene that produces enzymes that metabolize testosterone and dihydrotestosterone. Genetic body measurement may include CYP1A1 gene that produces enzymes that metabolize estrogens into 2 hydroxy-estrogen. Genetic body measurement may include CYP1B1 gene that produces enzymes that metabolize estrogens into 4 hydroxy-estrogen. Genetic body measurement may include CYP3A4 gene that produces enzymes that metabolize estrogen into 16 hydroxy-estrogen. Genetic body measurement may include COMT gene that produces enzymes that metabolize 2 hydroxy-estrogen and 4 hydroxy-estrogen into methoxy estrogen. Genetic body measurement may include GSTT1 gene that produces enzymes that eliminate toxic by-products generated from metabolism of estrogens. Genetic body measurement may include GSTM1 gene that produces enzymes responsible for eliminating harmful by-products generated from metabolism of estrogens. Genetic body measurement may include GSTP1 gene that produces enzymes that eliminate harmful by-products generated from metabolism of estrogens. Genetic body measurement may include SOD2 gene that produces enzymes that eliminate oxidant by-products generated from metabolism of estrogens.

With continued reference to FIG. 1, metabolic, as used herein, includes any process that converts food and nutrition into energy. Metabolic may include biochemical processes that occur within the body. Metabolic body measurement may include blood tests, hair tests, skin tests, amniotic fluid, buccal swabs and/or tissue test to identify a user's metabolism. Metabolic body measurement may include blood tests that examine glucose levels, electrolytes, fluid balance, kidney function, and liver function. Metabolic body measurement may include blood tests that examine calcium levels, albumin, total protein, chloride levels, sodium levels, potassium levels, carbon dioxide levels, bicarbonate levels, blood urea nitrogen, creatinine, alkaline phosphatase, alanine amino transferase, aspartate amino transferase, bilirubin, and the like.

With continued reference to FIG. 1, metabolic body measurement may include one or more blood, saliva, hair, urine, skin, and/or buccal swabs that examine levels of hormones within the body such as 11-hydroxy-androsterone, 11-hydroxy-etiocholanolone, 11-keto-androsterone, 11-keto-etiocholanolone, 16 alpha-hydroxyestrone, 2-hydroxyestrone, 4-hydroxyestrone, 4-methoxyestrone, androstanediol, androsterone, creatinine, DHEA, estradiol, estriol, estrone, etiocholanolone, pregnanediol, pregnanestriol, specific gravity, testosterone, tetrahydrocortisol, tetrahydrocrotisone, tetrahydrodeoxycortisol, allo-tetrahydrocortisol.

With continued reference to FIG. 1, metabolic body measurement may include one or more metabolic rate test results such as breath tests that may analyze a user's resting metabolic rate or number of calories that a user's body burns each day rest. Metabolic body measurement may include one or more vital signs including blood pressure, breathing rate, pulse rate, temperature, and the like. Metabolic body measurement may include blood tests such as a lipid panel such as low density lipoprotein (LDL), high density lipoprotein (HDL), triglycerides, total cholesterol, ratios of lipid levels such as total cholesterol to HDL ratio, insulin sensitivity test, fasting glucose test, Hemoglobin A1C test, adipokines such as leptin and adiponectin, neuropeptides such as ghrelin, pro-inflammatory cytokines such as interleukin 6 or tumor necrosis factor alpha, anti-inflammatory cytokines such as interleukin 10, markers of antioxidant status such as oxidized low-density lipoprotein, uric acid, paraoxonase 1. Persons skilled in the art, upon reviewing the entirety of this disclosure, will be aware of various additional examples of physiological state data that may be used consistently with descriptions of systems and methods as provided in this disclosure.

With continued reference to FIG. 1, physiological data may be obtained from a physically extracted sample. A "physical sample" as used in this example, may include any sample obtained from a human body of a user. A physical sample may be obtained from a bodily fluid and/or tissue analysis such as a blood sample, tissue, sample, buccal swab, mucous sample, stool sample, hair sample, fingernail sample and the like. A physical sample may be obtained from a device in contact with a human body of a user such as a microchip embedded in a user's skin, a sensor in contact with a user's skin, a sensor located on a user's tooth, and the like. Physiological data may be obtained from a physically extracted sample. A physical sample may include a signal from a sensor configured to detect physiological data of a user and record physiological data as a function of the signal. A sensor may include any medical sensor and/or medical device configured to capture sensor data concerning a patient, including any scanning, radiological and/or imaging device such as without limitation x-ray equipment, computer assisted tomography (CAT) scan equipment, positron emission tomography (PET) scan equipment, any form of magnetic resonance imagery (MRI) equipment, ultrasound equipment, optical scanning equipment such as photo-plethysmographic equipment, or the like. A sensor may include any electromagnetic sensor, including without limitation electroencephalographic sensors, magnetoencephalographic sensors, electrocardiogramansors, electromyographic sensors, or the like. A sensor may include a temperature sensor. A sensor may include any sensor that may be included in a mobile device and/or wearable device, including without limitation a motion sensor such as an inertial measurement unit (IMU), one or more accelerometers, one or more gyroscopes, one or more magnetometers, or the like. At least a wearable and/or mobile device sensor may capture step, gait, and/or other mobility data, as well as data describing activity levels and/or physical fitness. At least a wearable and/or mobile device sensor may detect heart rate or the like. A sensor may detect any hematological parameter including blood oxygen level, pulse rate, heart rate, pulse rhythm, blood sugar, and/or blood pressure. A sensor may be configured to detect internal and/or external biomarkers and/or readings. A sensor may be a part of apparatus 100 or may be a separate device in communication with apparatus 100. User data may include a profile, such as a psychological profile, generated using previous item selections by the user; profile may include, without limitation, a set of actions and/or navigational actions performed as described in further detail below, which may be combined with biological extraction data and/or other user data for processes as described in further detail below.

Physiological data and/or other data of each user may be stored, without limitation, in a user database. A user database may include any data structure for ordered storage and retrieval of data, which may be implemented as a hardware or software module. A user database may be implemented, without limitation, as a relational database, a key-value retrieval datastore such as a NOSQL database, or any other format or structure for use as a datastore that a person skilled in the art would recognize as suitable upon review of the entirety of this disclosure. A user database may include a plurality of data entries and/or records corresponding to user tests as described above. Data entries in a user database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a user database may reflect categories, cohorts, and/or populations of data consistently with this disclosure. A user database may be located in memory of computing device and/or on another device in and/or in communication with apparatus 100.

With continued reference to FIG. 1, in some embodiments, apparatus may be configured to classify user data 104 to a profile cluster 112. For the purposes of this disclosure, a "profile cluster" is a category including a plurality of related phenotypes. For example, in some embodiments, a profile cluster may include a grouping of phenotypes with similar nutritional needs. In some embodiments, user data 104 may be classified to a profile cluster 112 using a phenotype classifier. Phenotype classifier may be consistent with any classifier disclosed in this disclosure. In some embodiments, phenotype classifier may be generated using a machine-learning module, such as machine-learning module 300 disclosed with respect to FIG. 3. In some embodiments, phenotype classifier may be trained using training data correlating a plurality of user data to a plurality of profile clusters. Phenotype classifier may be configured to accept user data as input and to generate a profile cluster for the user data.

With continued reference to FIG. 1, in some embodiments, apparatus 100 may be configured to classify user data 104 to profile cluster 112 as a function of a profile cluster look-up table. In some embodiments, profile cluster lookup table may relate user data to profile clusters. In some embodiments, profile cluster lookup table may relate ranges of certain types of user data to profile clusters.

Still referring to FIG. 1, apparatus 100 may assign a user one or more cohort labels as a function of one or more phenotypic clusters. As used in this disclosure, "cohort label" is an identifier assigned to a user based on a phenotypic cluster. As a non-limiting example, cohort label may further classify a user within a phenotype group. In some embodiments, cohort label may be assigned once processor receives additional data. Additional data may provide more insight to a health status of a user. In some instances, cohort label may be assigned as a function of a biological extraction. As a non-limiting example, cohort label may be "diabetic" when biological extraction data indicates a high blood sugar. apparatus 100 may reference a cohort label lookup table to assign a cohort label to a user. In some embodiments, cohort label may have a biological extraction threshold. As a non-limiting example, apparatus 100 may assign a user a "anemic" when a user's iron levels fall below a threshold.

Still referring to FIG. 1, in some embodiments, apparatus 100 may be configured to receive edible data 108. "Edible data" as used in this disclosure is information relating to consumable items. In some embodiments, edible data 108 may include a meal identification. A "meal identification," also referred to as meal ID, as used in this disclosure, is a classification of a recipe. In some embodiments, apparatus 100 may receive edible data 108 and/or a meal ID from a user. In some embodiments, a meal ID of edible data 108 may include a title and/or a description related to a meal. For example a meal ID may include a name of a dish, such as "Beef Stroganoff". A description of a meal ID may include one or more general contents of a dish and/or a specific description of the dish. For example, a description may include data that Beef Stroganoff is an originally Russian dish of sautéed pieces of beef served in a sauce of mustard and smetana (sour cream). Still referring to FIG. 1, apparatus 100 is configured to receive recipe data containing nutrient data from the user. Recipe data may include a list of nutrients to prepare a meal. For example, and without limitation, edible data 108 may include nutrients in a beef stroganoff dish, which may include: 1 pound uncooked wide egg noodles, ¼ cup butter, divided, 2½ pounds thinly-sliced steak, fine sea salt and freshly-cracked black pepper, 4.5 small white onions, thinly sliced, 3 pound sliced mushrooms, 2 cloves garlic, minced or pressed, ½ cup dry white wine, 1½ cups beef stock, 1 tablespoon Worcestershire sauce, 3 tablespoons all-purpose flour, ½ cup of sour cream, and chopped fresh parsley.

Still referring to FIG. 1, in some embodiments, apparatus 100 may extract plurality of nutrients 116 from edible data 108. "Nutrients," as used in this disclosure, are elements of a meal. Nutrients 116 may include, but are not limited to, meats, vegetables, sauces, syrups, seafoods, fruits, dairy products, and the like. In some embodiments, apparatus 100 may utilize a language processing module to extract a plurality of nutrients 116 from edible data 108. A language processing module may include any hardware and/or software module. A language processing module may be configured to extract, from the one or more documents, one or more words, letters, characters, and the like, without limitation. One or more words may include, without limitation, strings of one or more characters, including without limitation any sequence or sequences of letters, numbers, punctuation, diacritic marks, engineering symbols, geometric dimensioning and tolerancing (GD&T) symbols, chemical symbols and formulas, spaces, whitespace, and other symbols, including any symbols usable as textual data as described above. Textual data may be parsed into tokens, which may include a simple word (sequence of letters separated by whitespace) or more generally a sequence of characters as described previously. The term "token," as used herein, refers to any smaller, individual groupings of text from a larger source of text; tokens may be broken up by word, pair of words, sentence, or other delimitation. These tokens may in turn be parsed in various ways. Textual data may be parsed into words or sequences of words, which may be considered words as well. Textual data may be parsed into "n-grams", where all sequences of n consecutive characters are considered. Any or all possible sequences of tokens or words may be stored as "chains", for example for use as a Markov chain or Hidden Markov Model.

Still referring to FIG. 1, a language processing module may operate to produce a language processing model. A language processing model may include a program automatically generated by computing device and/or a language processing module to produce associations between one or more words extracted from at least a document and detect associations, including without limitation mathematical associations, between such words. Associations between language elements, where language elements include for purposes herein extracted words, relationships of such categories to other such term may include, without limitation, mathematical associations, including without limitation statistical correlations between any language element and any other language element and/or language elements. Statistical correlations and/or mathematical associations may include probabilistic formulas or relationships indicating, for instance, a likelihood that a given extracted word indicates a given category of semantic meaning. As a further example, statistical correlations and/or mathematical associations may include probabilistic formulas or relationships indicating a positive and/or negative association between at least an extracted word and/or a given semantic meaning; positive or negative indication may include an indication that a given document is or is not indicating a category semantic meaning. Whether a phrase, sentence, word, or other textual element in a document or corpus of documents constitutes a positive or negative indicator may be determined, in an embodiment, by mathematical associations between detected words, comparisons to phrases and/or words indicating positive and/or negative indicators that are stored in memory at computing device, or the like. In some embodiments, language processing module may be configured to identify tokens corresponding to nutrients or categories of nutrients within a corpus of text. Language processing module may be trained using training data containing a plurality of tokens representing nutrients and/or categories of nutrients. In some embodiments, the language processing module training data may include input texts correlated to tokens representing nutrients and/or categories of nutrients extracted from those texts.

Still referring to FIG. 1, a language processing module and/or diagnostic engine may generate the language processing model by any suitable method, including without limitation a natural language processing classification algorithm; a language processing model may include a natural language process classification model that enumerates and/or derives statistical relationships between input terms and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated. In an alternative or additional approach, sequential tokens may be modeled as chains, serving as the observations in a Hidden Markov Model (HMM). HMMs as used herein are statistical models with inference algorithms that that may be applied to the models. In such models, a hidden state to be estimated may include an association between an extracted words, phrases, and/or other semantic units. There may be a finite number of categories to which an extracted word may pertain; an HMM inference algorithm, such as the forward-backward algorithm or the Viterbi algorithm, may be used to estimate the most likely discrete state given a word or sequence of words. Language processing module may combine two or more approaches. For instance, and without limitation, machine-learning program may use a combination of Naive-Bayes (NB), Stochastic Gradient Descent (SGD), and parameter grid-searching classification techniques; the result may include a classification algorithm that returns ranked associations.

Continuing to refer to FIG. 1, generating a language processing model may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element. Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors. Degree of similarity may include any other geometric measure of distance between vectors.

Still referring to FIG. 1, a language processing module may use a corpus of documents to generate associations between language elements in a language processing module, and diagnostic engine may then use such associations to analyze words extracted from one or more documents and determine that the one or more documents indicate significance of a category. In an embodiment, language module and/or apparatus 100 may perform this analysis using a selected set of significant documents, such as documents identified by one or more experts as representing good information; experts may identify or enter such documents via graphical user interface, or may communicate identities of significant documents according to any other suitable method of electronic communication, or by providing such identity to other persons who may enter such identifications into apparatus 100. Documents may include recipes, nutrient lists, nutritional facts, or the like. Documents may include words and alphanumeric character strings associated with edible data. Documents may include words and alphanumeric character strings associated with nutrient data. Documents may be entered into a computing device by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, diagnostic engine may automatically obtain the document using such an identifier, for instance by submitting a request to a database or compendium of documents such as JSTOR as provided by Ithaka Harbors, Inc. of New York.

Still refereeing to FIG. 1, in some embodiments, apparatus 100 may utilize optical character recognition to identify and/or extract plurality of nutrients 116 from edible data 108. Optical character recognition or optical character reader (OCR) includes automatic conversion of images of written (e.g., typed, handwritten or printed text) into machine-encoded text. In some cases, recognition of at least a keyword from an image component may include one or more processes, including without limitation optical character recognition (OCR), optical word recognition, intelligent character recognition, intelligent word recognition, and the like. In some cases, OCR may recognize written text, one glyph or character at a time. In some cases, optical word recognition may recognize written text, one word at a time, for example, for languages that use a space as a word divider. In some cases, intelligent character recognition (ICR) may recognize written text one glyph or character at a time, for instance by employing machine learning processes. In some cases, intelligent word recognition (IWR) may recognize written text, one word at a time, for instance by employing machine learning processes.

Still referring to FIG. 1, in some cases OCR may be an "offline" process, which analyses a static document or image frame. In some cases, handwriting movement analysis can be used as input to handwriting recognition. For example, instead of merely using shapes of glyphs and words, this technique may capture motions, such as the order in which segments are drawn, the direction, and the pattern of putting the pen down and lifting it. This additional information can make handwriting recognition more accurate. In some cases, this technology may be referred to as "online" character recognition, dynamic character recognition, real-time character recognition, and intelligent character recognition.

Still referring to FIG. 1, in some cases, OCR processes may employ pre-processing of image component. Pre-processing process may include without limitation de-skew, de-speckle, binarization, line removal, layout analysis or "zoning," line and word detection, script recognition, character isolation or "segmentation," and normalization. In some cases, a de-skew process may include applying a transform (e.g., homography or affine transform) to image component to align text. In some cases, a de-speckle process may include removing positive and negative spots and/or smoothing edges. In some cases, a binarization process may include converting an image from color or greyscale to black-and-white (i.e., a binary image). Binarization may be performed as a simple way of separating text (or any other desired image component) from a background of image component. In some cases, binarization may be required for example if an employed OCR algorithm only works on binary images. In some cases, a line removal process may include removal of non-glyph or non-character imagery (e.g., boxes and lines). In some cases, a layout analysis or "zoning" process may identify columns, paragraphs, captions, and the like as distinct blocks. In some cases, a line and word detection process may establish a baseline for word and character shapes and separate words, if necessary. In some cases, a script recognition process may, for example in multilingual documents, identify script allowing an appropriate OCR algorithm to be selected. In some cases, a character isolation or "segmentation" process may separate signal characters, for example character-based OCR algorithms. In some cases, a normalization process may normalize aspect ratio and/or scale of image component.

Still referring to FIG. 1, in some embodiments an OCR process will include an OCR algorithm. Exemplary OCR algorithms include matrix matching process and/or feature extraction processes. Matrix matching may involve comparing an image to a stored glyph on a pixel-by-pixel basis. In some case, matrix matching may also be known as "pattern matching," "pattern recognition," and/or "image correlation." Matrix matching may rely on an input glyph being correctly isolated from the rest of the image component. Matrix matching may also rely on a stored glyph being in a similar font and at a same scale as input glyph. Matrix matching may work best with typewritten text.

Still referring to FIG. 1, in some embodiments, an OCR process may include a feature extraction process. In some cases, feature extraction may decompose a glyph into features. Exemplary non-limiting features may include corners, edges, lines, closed loops, line direction, line intersections, and the like. In some cases, feature extraction may reduce dimensionality of representation and may make the recognition process computationally more efficient. In some cases, extracted feature can be compared with an abstract vector-like representation of a character, which might reduce to one or more glyph prototypes. General techniques of feature detection in computer vision are applicable to this type of OCR. In some embodiments, machine-learning process like nearest neighbor classifiers (e.g., k-nearest neighbors algorithm) can be used to compare image features with stored glyph features and choose a nearest match. OCR may employ any machine-learning process described in this disclosure. Exemplary non-limiting OCR software includes Cuneiform and Tesseract. Cuneiform is a multi-language, open-source optical character recognition system originally developed by Cognitive Technologies of Moscow, Russia.

Tesseract is free OCR software originally developed by Hewlett-Packard of Palo Alto, California, United States.

Still referring to FIG. 1, in some cases, OCR may employ a two-pass approach to character recognition. Second pass may include adaptive recognition and use letter shapes recognized with high confidence on a first pass to recognize better remaining letters on the second pass. In some cases, two-pass approach may be advantageous for unusual fonts or low-quality image components where visual verbal content may be distorted. Another exemplary OCR software tool include OCRopus. OCRopus development is led by German Research Centre for Artificial Intelligence in Kaiserslautern, Germany. In some cases, OCR software may employ neural networks.

Still referring to FIG. 1, in some cases, OCR may include post-processing. For example, OCR accuracy can be increased, in some cases, if output is constrained by a lexicon. A lexicon may include a list or set of words that are allowed to occur in a document. In some cases, a lexicon may include, for instance, all the words in the English language, or a more technical lexicon for a specific field. In some cases, an output stream may be a plain text stream or file of characters. In some cases, an OCR process may preserve an original layout of visual verbal content. In some cases, near-neighbor analysis can make use of co-occurrence frequencies to correct errors, by noting that certain words are often seen together. For example, "Washington, D.C." is generally far more common in English than "Washington DOC." In some cases, an OCR process may make us of a priori knowledge of grammar for a language being recognized. For example, grammar rules may be used to help determine if a word is likely to be a verb or a noun. Distance conceptualization may be employed for recognition and classification. For example, a Levenshtein distance algorithm may be used in OCR post-processing to further optimize results.

Still referring to FIG. 1, in some embodiments, edible data 108 may be provided by a user, such as, but not limited to, a chef, line cook, an individual, and the like. Edible data 108 may be received and/or stored by a graphical user interface or a user database as described further below. Alternatively or additionally, apparatus 100 may retrieve edible data 108 from an online repository or other suitable source for retrieving information regarding meal preparation. In non-limiting illustrative examples, edible data 108 may contain sequentially ordered tasks that may be sequentially ordered based upon a chronological order, tasks ordered by resource optimization, and the like. Edible data 108 may contain elements, steps, instructions, or the like that refer to preparing one or more meals, by one or more personnel, using one of more stations, appliances, utensils, and the like. In non-limiting illustrative examples, apparatus 100 may retrieve a plurality of edible data 108 by retrieving a series of steps corresponding to a meal ID, for instance and without limitation, recipe steps using available nutrients 116 for cooking a beef stew. In further non-limiting illustrative examples, the steps to a beef stew may be associated with a chronological sequential ordering of personnel tasks, nutrient retrieval, kitchen space use, and may differ based upon time constraints, including and/or avoiding certain nutrients 116, equipment, and the like.

Still referring to FIG. 1, in some embodiments, apparatus 100 may be configured to generate a web search. A "web search" as used in this disclosure is a query for information through the Internet. Generating a web search may include generating a web crawler function. A web search may be configured to search for one or more keywords, key phrases, and the like. A keyword may be used by a query to filter potential results from a query. As a non-limiting example, a keyword may include "Gluten". A query may be configured to generate one or more key words and/or phrases as a function of edible data 108. A query may give a weight to one or more semantic elements of edible data 108. "Weights", as used herein, may be multipliers or other scalar numbers reflecting a relative importance of a particular attribute or value. A weight may include, but is not limited to, a numerical value corresponding to an importance of an element. In some embodiments, a weighted value may be referred to in terms of a whole number, such as 1, 100, and the like. As a non-limiting example, a weighted value of 0.2 may indicate that the weighted value makes up 20% of the total value. As a non-limiting example, edible data 108 may include the words "gluten free". A query may give a weight of 0.8 to the word "gluten", and a weight of 0.2 to the word "free". A query may map a plurality of semantic elements of query results having similar elements to the word "gluten" with differing elements than the word "free" due to the lower weight value paired to the word "gluten". In some embodiments, a query may pair one or more weighted values to one or more semantic elements of edible data 108. Weighted values may be tuned through a machine-learning model, such as any machine learning model as described throughout this disclosure without limitation. In some embodiments, a query may generate weighted values based on prior queries. In some embodiments, a query may be configured to filter out one or more "stop words" that may not convey meaning, such as "of," "a," "an," "the," or the like.

Still referring to FIG. 1, in some embodiments, apparatus 100 may generate an index classifier. In an embodiment, an index classifier may include a classifier. A "classifier," as used in this disclosure is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. An index classifier may include a classifier configured to input semantic elements and output web search indices. A "web search index," as defined in this disclosure is a data structure that stores uniform resource locators (URLs) of web pages together with one or more associated data that may be used to retrieve URLs by querying the web search index; associated data may include keywords identified in pages associated with URLs by programs such as web crawlers and/or "spiders." A web search index may include any data structure for ordered storage and retrieval of data, which may be implemented as a hardware or software module. A web search index may be implemented, without limitation, as a relational database, a key-value retrieval datastore such as a NOSQL database, or any other format or structure for use as a datastore that a person skilled in the art would recognize as suitable upon review of the entirety of this disclosure. Data entries in a web search index may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a web search index may reflect categories, cohorts, and/or populations of data consistently with this disclosure. In an embodiment, a web search query at a search engine may be submitted as a query to a web search index, which may retrieve a list of URLs responsive to the query. In some embodiments, apparatus 100 may be configured to generate a query based on a freshness and/or age of a query result. A freshness may include an accuracy of a query result. An age may include a metric of how outdated a query result may be. In some embodiments, apparatus 100 may generate a web crawler configured to search the Internet for edible data 108, such as, but not limited to, nutrients 116, preparation steps, category of food, allergen data, and the like. As a non-limiting example, a query may include a web crawler configured to search and/or index information of words and/or phrases having a similarity to edible data 108.

Still referring to FIG. 1, in some embodiments, edible data 108 may include nutrient data. "Nutrient data," as used in this disclosure, is information pertaining to the nutritional value of one or more nutrients 116. In some embodiments, nutrient data may include nutritional values related to nutrients 116 in a meal. For example, nutritional values may include the value of vitamin, caloric, protein, fat, cholesterol, sugar, carbohydrate, sodium, and the like in the meal. For example, in beef stroganoff, the nutritional values may be calories 235, total fat 11 g, saturated fat 6 g, cholesterol 50 mg, sodium 1,044 mg, potassium 336 mg, total carbohydrate 22 g, dietary fiber 1.4 g, sugar 4 g, protein 12 g, vitamin c. In some embodiments, nutritional values may include a daily value of nutrients 116 in a dish. "Daily value (DV)," as used in this disclosure, is the recommended amount of nutrients 116 a person should consume and not to exceed each day. The % DV may be how much a nutrient in a single serving of an individual dish or dietary supplement contributes to a daily diet. For example, if the DV for a certain nutrient is 300 micrograms (mcg) and a dish or supplement has 30 mcg in one serving, the % DV for that nutrient in a serving of the product may be 10%. In some embodiments, apparatus 100 may receive recipe data from a user database. User database may contain recipe data received from a plurality of different users categorized to a common meal ID. For example, user database may contain a recipe data table containing a plurality of different recipes and nutritional values common for a beef stroganoff dish.

Still referring to FIG. 1, in some embodiments, apparatus 100 may be configured to classify plurality of nutrients 116 to impact factors 120. An "impact factor," as used in this disclosure, is a metric of influence one or more nutrients 116 has on an individual's biological system. A "biological system" as used in this disclosure is a process and/or group of processes that occur in an individuals physiology. Impact factors 120 may include, without limitation, concentration of nutrients 116, quantity of nutrients 116, calories of nutrients 116, allergens associated with one or more nutrients 116, carbohydrate and/or other macronutrient quantities, ratios, and the like. In some embodiments, impact factors 120 may be based on essential macronutrients and micronutrients. "Micronutrients," as used herein, are nutrients that a person needs in small doses. For example, micronutrients may include vitamins and minerals. "Macronutrients," as used herein, are nutrients that a person needs in larger amounts. For example, macronutrients may include water, protein, carbohydrates, and fats. In some embodiments, impact factors 120 may be based on nutrients 116 essential for boosting the immune system, helping prevent or delay certain cancers, such as prostate cancer, strengthening teeth and bones, aiding in calcium absorption, maintaining healthy skin, helping the body metabolize proteins and carbs, supporting healthy blood, burning fat, building muscle, maintaining healthy weight, losing water weight, aiding brain and nervous system functioning, aiding in blood clotting, helping to carry oxygen and/or the like. A user may select, through GUI 128, what impact factors 120 may be based on. In some embodiments, a user may select a plurality of impact factors 120. In some embodiments, receive impart factor data in the form of documents, medical papers, research papers, and the like through an impact factors 120 database. "Impact factor database," as used in this disclosure, is a data structure containing information related to a plurality of impact factors 120. An impact factor database may be populated by apparatus 100 utilizing a web crawler. An impact factor database may be populated by expert submission. An "expert," as used herein, is a person who has a comprehensive and authoritative knowledge of or skill in a particular area. For example, a doctor may submit a paper on how fish oil aids in preventing cancer. An expert submission may include a single expert submission and/or a plurality of submissions from an expert; plurality of submissions may be received from a plurality of experts as described in U.S. patent application Ser. No. 16/397,814, filed, Apr. 29, 2019, and titled "METHODS AND SYSTEMS FOR CLASSIFICATION USING EXPERT DATA", of which is incorporated by reference herein in its entirety.

Still referring to FIG. 1, in some embodiments, apparatus 100 may determine one or more impact factors 120 for one or more phenotypes. A "phenotype," as used in this disclosure, is a composite observable characteristic or trait of an individual. A phenotype may include a user's biochemical and physiological properties, behavior, and products of behavior. Behavioral phenotypes may include cognitive, personality, and behavior patterns. This may include effects on cellular and physiological phenotypic traits that may occur due to external or environmental factors. For example, DNA methylation and histone modification may alter phenotypic expression of genes without altering underlying DNA sequence. Phenotype may include a congenital disorder, anomaly, and the like, such as hearing defects, trisomy 18 (Edward's syndrome), trisomy 21 (down syndrome), trisomy 13 (Patau syndrome), cleft palate, spina bifida, phenylketonuria, glutamate carboxypeptidase II mutation, pyloric stenosis, congenital hip dislocation, anencephaly, hypoplasia, Meckel's diverticulum, and the like. Phenotype may include a genotype-environment interaction (GxE). Phenotype may include any diagnosis (current disorder) and/or prognosis (predicted difficulty, future diagnosis, outcome, and the like) associated with a congenital factor. Phenotype may include identifiers associated with disorders, conditions, symptoms, and the like, which may correspond with categorization. Phenotype may include a predictive classification, where a subject may be considered reasonably healthy at birth, does not harbor congenital factor(s) indicative of obvious current congenital disorder but may include data that indicates a phenotype with which they may be most closely categorized to, and/or an imminent categorization. A phenotype may be stored and/or retrieved from a user database.

Still referring to FIG. 1, in some embodiments, apparatus 100 may classify plurality of nutrients 116 to impact factors 120 utilizing a nutrient classifier. A "classifier," as used in this disclosure is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. A nutrient classifier may be configured to output at least a datum that labels or otherwise identifies a set of data that are clustered together, found to be close under a distance metric as described below, or the like. In some embodiments, a nutrient classifier may receive meal ID and recipe data as an input and output a plurality of matched nutrient data elements to an importance factor. For example, a nutrient classifier may match nutrients 116 in a dish that contain a nutritional value that are essential for boosting the immune system. In some embodiments, a nutrient classifier may receive meal ID and recipe data as an input and output a plurality of matched nutrient data elements to a plurality of impact factors. For example, a nutrient classifier may match nutrients 116 in a dish that contain a nutritional value that are essential for boosting the immune system, building muscle, maintaining healthy skin, and the like. Training data for a nutrient classifier may include data from impact factor data. For example, classification based on muscle building may include training data containing documents and expert submission exemplifying nutrients 116 that may correlate to muscle building. In some embodiments, training data may include, a plurality of recipe data received from a plurality of user from user database.

Still referring to FIG. 1, in some embodiments, apparatus 100 may receive edible data 108 and/or a meal ID from a user database. A "user database," as used in this disclosure is a data structure contain information uploaded by a user. User database may contain information from a plurality of different users categorized to a common meal ID. For example, user database may contain a meal ID table containing a plurality of different titles common for a beef stroganoff dish and a plurality of different meal descriptions associated to the dish. User database and all other databases in this disclosure may be implemented, without limitation, as a relational user database, a key-value retrieval user database such as a NOSQL user database, or any other format or structure for use as a user database that a person skilled in the art would recognize as suitable upon review of the entirety of this disclosure. User database may alternatively or additionally be implemented using a distributed data storage protocol and/or data structure, such as a distributed hash table or the like. User database may include a plurality of data entries and/or records as described above. Data entries in a user database may be flagged with or linked to one or more additional elements of information, which may be reflected in data entry cells and/or in linked tables such as tables related by one or more indices in a relational user database. Persons skilled in the art, upon reviewing the entirety of this disclosure, will be aware of various ways in which data entries in a user database may store, retrieve, organize, and/or reflect data and/or records as used herein, as well as categories and/or populations of data consistently with this disclosure. A user database may include one or more elements of edible data 108 and/or user data. In some embodiments, a user database may be populated through user input and/or one or more web searches.

Still referring to FIG. 1, in some embodiments, a nutrient classifier may be further configured to generate nutrient score 124. A "nutrient score" as used in this disclosure is a value given to a nutrient. A nutrient classifier may score plurality of nutrients 116. A nutrient classifier may score plurality of nutrients 116 across a plurality of phenotypes to determine an impact factor of impact factors 120. In some instances, nutrient classifier may be trained using nutrient classifier training data. In some embodiments, nutrient classifier training data may include historical nutrient data correlated to categories of nutrients. In some embodiments, nutrient classifier training data may contain categories of nutrients correlated to scores for those categories of nutrients. In some embodiments, a lookup table correlating categories of nutrients to nutrient scores 124 may be used to determine a nutrient score 124 once nutrient classifier determines a category of nutrient. In some embodiments, a nutrient classifier may be configured to score a plurality of nutrients 116 of plurality of nutrients 116. Nutrient scores 124 may be based off, without limitation, relative impact of one or more nutrients on one or more phenotypes. For instance, and without limitation, a score of 3 out of 10 may be assigned to a filet mignon for a phenotype of vegan. In some embodiments, a score may be based off a nutrition target range. In some embodiments, nutrient score 124 may be generated by using an objective function as described in further detail below. It should be noted the nutrient score 124 may be generated using an objective function that is optimized using impact factors as constraints. In some instances, objective function may be optimized using profile clusters as constraints.

Still referring to FIG. 1, apparatus 100 may be configured to receive and/or determine a nutrition target range of one or more users, profile clusters 112, and the like. A "nutrition target range," as used in this disclosure, is a value or range of values of quantities of nutrients 116. Apparatus 100 may utilize a nutrient target machine learning model to determine a nutrient target range of one or more individuals. A nutrient target machine learning model may be trained with training data correlating user data to nutrition target ranges. In some instances, training data may correlate a biological extractions and/or phenotypes to target ranges. In some instances, training data may correlate a user profiles to target ranges. Training data may be received through user input, external computing devices, and/or previous iterations of processing. In some instances, training data may be retrieved from a database storing user data correlated to target ranges. As a non-limiting example, training data may be stored in a training data lookup table (LUT). As used in this disclosure, a "lookup table" is an array of data that maps input values to output values. A lookup table may be used to replace a runtime computation with an array indexing operation. In another non limiting example, a training data look up table may be able to relate user data to target ranges. In some embodiments, a nutrient classifier and/or apparatus 100 may utilize a nutrient target machine learning model. A nutrient target machine learning model may be configured to receive user data and/or edible data 108 and output one or more nutrient target ranges of one or more individuals and/or groups of individuals.

Apparatus 100 may utilize a nutrient score machine learning model to determine a nutrient score of at least a nutrient. A nutrient score machine learning model may be trained with training data correlating phenotype data to nutrient scores. Training data may be received through user input, external computing devices, and/or previous iterations of processing. In some instances, training data may be retrieved from a database storing user data correlated to target ranges. As a non-limiting example, training data may be stored in a training data lookup table (LUT).

Still referring to FIG. 1, computing device may be configured to generate a nutrition supplement as a function of the nutrition range target. A "nutrition supplement," as used in this disclosure, is a modification of a recipe. Nutritional supplements may include, without limitation, different sets of nutrients 116, such as spices, meats, seasonings, vitamin powders, and the like. In some embodiments, a nutrient classifier may be configured to receive training data correlating recipe data and/or user data to one or more nutritional supplements. Training data may be received through user, external computing devices, and/or previous iterations of processing. A nutrient classifier may input edible data 108 and/or user data and output one or more nutritional supplements. suggested by computing device that offer nutritional values aligned to nutrition range target.

Still referring to FIG. 1, in some embodiments, apparatus 100 may be configured to generate nutrient chain. An "nutrient chain" as used in this disclosure is a set of edible items. Edible items may include, without limitation, seasonings, spices, vitamin powders, meats, seafood, fruits, vegetables, dairy products, and the like. In some embodiments, apparatus 100 may compare impact factors 120 with plurality of nutrients 116 to generate nutrient chain. In some embodiments, apparatus 100 may be configured to compare any data as described throughout this disclosure using an objective function. For instance, apparatus 100 may generate an objective function. An "objective function" as used in this disclosure is a process of minimizing or maximizing one or more values based on a set of constraints. In some embodiments, an objective function of apparatus 100 may include an optimization criterion. An optimization criterion may include any description of a desired value or range of values for one or more impact factors; desired value or range of values may include a maximal or minimal value, a range between maximal or minimal values, or an instruction to maximize or minimize an impact factor. As a non-limiting example, an optimization criterion may specify that an impact factor should be within a 1% difference of an optimization criterion. An optimization criterion may alternatively request that an impact factor be greater than a certain value. An optimization criterion may specify one or more tolerances for differences in macronutrients of one or more nutrients 116 in a recipe. An optimization criterion may specify one or more desired impact factor criteria for a nutrient chain. In an embodiment, an optimization criterion may assign weights to different impact factors or values associated with impact factors. One or more weights may be expressions of value to a user of a particular outcome, impact factor value, or other facet of an nutrient chain. Optimization criteria may be combined in weighted or unweighted combinations into a function reflecting an overall outcome desired by a user; function may be an nutrient chain function to be minimized and/or maximized. A function may be defined by reference to impact factor criteria constraints and/or weighted aggregation thereof as provided by apparatus 100; for instance, an impact factor function combining optimization criteria may seek to minimize or maximize a function of nutrient chain generation.

Still referring to FIG. 1, generation of an objective function may include generation of a function to score and weight factors to achieve a process score for each feasible pairing. In some embodiments, pairings may be scored in a matrix for optimization, where columns represent nutrients 116 and rows represent impact factors potentially paired therewith; each cell of such a matrix may represent a score of a pairing of the corresponding nutrient to the corresponding impact factor. In some embodiments, assigning a predicted process that optimizes the objective function includes performing a greedy algorithm process. A "greedy algorithm" is defined as an algorithm that selects locally optimal choices, which may or may not generate a globally optimal solution. For instance, apparatus 100 may select pairings so that scores associated therewith are the best score for each impact factor and/or for each nutrient. In such an example, optimization may determine the combination of nutrients 116 such that each impact factor pairing includes the highest score possible.

Still referring to FIG. 1, an objective function may be formulated as a linear objective function. Apparatus 100 may solve an objective function using a linear program such as without limitation a mixed-integer program. A "linear program," as used in this disclosure, is a program that optimizes a linear objective function, given at least a constraint. For instance, and without limitation, objective function may seek to maximize a total score $\Sigma_{r \in R} \Sigma_{s \in S} c_{rs} x_{rs}$, where R is a set of all nutrients 116 $r$, S is a set of all impact factors $s$, $c_{rs}$ is a score of a pairing of a given nutrient with a given impact factor, and $x_{rs}$ is 1 if an nutrient r is paired with an impact factor s, and 0 otherwise. Continuing the example, constraints may specify that each nutrient is assigned to only one impact factor, and each impact factor is assigned only one nutrient. Impact factors may include nutrients 116 as described above. Sets of nutrients 116 may be optimized for a maximum score combination of all generated nutrients 116. In various embodiments, apparatus 100 may determine a combination of nutrients 116 that maximizes a total score subject to a constraint that all nutrients 116 are paired to exactly one impact factor. Not all impact factors may receive an nutrient pairing since each impact factor may only produce one nutrient pairing. In some embodiments, an objective function may be formulated as a mixed integer optimization function. A "mixed integer optimization" as used in this disclosure is a program in which some or all of the variables are restricted to be integers. A mathematical solver may be implemented to solve for the set of feasible pairings that maximizes the sum of scores across all pairings; mathematical solver may be implemented on apparatus 100, another device, and/or may be implemented on third-party solver.

With continued reference to FIG. 1, optimizing an objective function may include minimizing a loss function, where a "loss function" is an expression an output of which an optimization algorithm minimizes to generate an optimal result. As a non-limiting example, apparatus 100 may assign variables relating to a set of parameters, which may correspond to score nutrients 116 as described above, calculate an output of mathematical expression using the variables, and select a pairing that produces an output having the lowest size, according to a given definition of "size," of the set of outputs representing each of a plurality of nutrients 116 and/or impact factors; size may, for instance, included absolute value, numerical size, or the like. Selection of different loss functions may result in identification of different potential pairings as generating minimal outputs. Objectives represented in an objective function and/or loss function may include minimization of impact factors. Objectives may include minimization of preparation time of a recipe. Objectives may include minimization of costs of a recipe. Objectives may include maximization of compatibility across a wide range of individuals.

Still referring to FIG. 1, in some embodiments, apparatus 100 may receive a meal ID through a graphical user interface (GUI) 128. A "graphical user interface" as used in this disclosure is an interface including a set of one or more pictorial and/or graphical icons corresponding to one or more computer actions. GUI 128 may be configured to receive user input, as described above. GUI 128 may include one or more event handlers. In some embodiments, GUI 128 may be configured to display outputs. In some instances, GUI 128 may display a score of nutrient 116. An "event handler" as used in this disclosure is a callback routine that operates asynchronously once an event takes place. Event handlers may include, without limitation, one or more programs to perform one or more actions based on user input, such as generating pop-up windows, submitting forms, changing background colors of a webpage, and the like. Event handlers may be programmed for specific user input, such as, but not limited to, mouse clicks, mouse hovering, touchscreen input, keystrokes, and the like. For instance and without limitation, an event handler may be programmed to generate a pop-up window if a user double clicks on a specific icon. User input may include, a manipulation of computer icons, such as, but not limited to, clicking, selecting, dragging and dropping, scrolling, and the like. In some embodiments, user input may include an entry of characters and/or symbols in a user input field. A "user input field" as used in this disclosure is a portion of a graphical user interface configured to receive data from an individual. A user input field may include, but is not limited to, text boxes, search fields, filtering fields, and the like. In some embodiments, user input may include touch input. Touch input may include, but is not limited to, single taps, double taps, triple taps, long presses, swiping gestures, and the like. One of ordinary skill in the art will appreciate the various ways a user may interact with GUI 128. In some embodiments, GUI 128 may be consistent with graphical user interfaces as described in U.S. patent application Ser. No. 17/062,740, filed Oct. 5, 2020, and titled "METHODS AND SYSTEMS FOR ARRANGING AND DISPLAYING GUIDED RECOMMENDATIONS VIA A USER INTERFACE BASED ON BIOLOGICAL EXTRACTION", of which is incorporated by reference herein in its entirety.

Continuing in reference to FIG. 1, apparatus 100 may retrieve a plurality of nutrient chain, wherein retrieving an nutrient chain may include retrieving, for each meal of the plurality of meals, an nutrient chain identifying a plurality of sequentially ordered tasks for preparation of the meal. An nutrient chain may be provided by a user, such as a restaurant, cook, or the like, and nutrient chains may be stored and/or retrieved by apparatus 100 from a meal database, for instance from an nutrient chain database. Alternatively or additionally, apparatus 100 may retrieve nutrient chain from an online repository or other suitable source for retrieving information regarding meal preparation. In non-limiting illustrative examples, an nutrient chain may contain sequentially ordered tasks that may be sequentially ordered based upon a chronological order, tasks ordered by resource optimization, task ordered by customer priority, and the like. An nutrient chain may contain elements, steps, instructions, or the like that refer to preparing one or more meals, by one or more personnel, using one of more stations, appliances, utensils, and the like. Apparatus 100 may store and/or retrieve nutrient chain, or an element of an existing nutrient chain to form a new nutrient chain, from a meal database, online repository, blog, culinary website, or any other suitable source, as described above. In non-limiting illustrative examples, apparatus 100 may retrieve a plurality of nutrient chain by retrieving a series of steps corresponding to an identification of a meal of edible data 108, for instance and without limitation, recipe steps using available nutrients 116 for cooking a beef stew. In further non-limiting illustrative examples, the steps to a beef stew may be associated with a chronological sequential ordering of personnel tasks, nutrient retrieval, kitchen space use, and may differ based upon time constraints, including and/or avoiding certain nutrients 116, equipment, and the like.

Continuing in reference to FIG. 1, apparatus 100 may retrieve a plurality of nutrient chain, wherein retrieving may include identifying, for each nutrient chain, a resource list identifying a plurality of resources, wherein each resource is associated with a task of the plurality of sequentially ordered tasks. A "resource list," as described in this disclosure refers to a tabulation, list, or the like, of nutrient identities, amounts, and expirations; kitchen stations, equipment, appliances, utensils, dishware, personnel, operating hours, tables, customers; delivery couriers including restaurant employees and secondary couriers via application services, 'gig' economy services, and the like; delivery vehicles, including cars, trucks, bikes, and the like, and any other suitable resource relating the preparation of a meal, delivery of a meal, and/or meal orders. Apparatus 100 may determine a resource and tabulate, list, group, or otherwise categorize a plurality of resources by retrieving a resource form a database, as described above. Alternatively or additionally, a resource of a resource list may be stored and/or retrieved from a database by a machine-learning process, such as a first machine-learning model, as a resource may correspond to a plurality of meals, nutrients 116, nutrient chains, or the like.

Still referring to FIG. 1, in some embodiments, apparatus 100 may retrieve and/or generate a plurality of nutrient chain. Nutrient chain may differ at branching points that correspond to different pathways, series of elements, steps, or the like in preparing a meal. In non-limiting illustrations a branch point may represent places where deviations in tasks in an nutrient chain may differ for instance, omitting or including a step to eliminate or add a new nutrient, for instance removing onions from the beef stew upon customer request, or customizing meal by adding chives. In further non-limiting illustrative examples, a branch point may represent a place in an nutrient chain where concurrently performed steps are added, subtracted, combined, or split into new nutrient chain. For instance and without limitation, a branch point may include a beginning preparation of a beef stock for a meal, a first kitchen personnel may include next any series of vegetables, beginning with any of the four, before moving to a next task in the nutrient chain. In such an example, several nutrient chain modifications may be introduced at the branch point, for instance and without limitation, a second kitchen personnel may be added to assist in the nutrient preparation steps to decrease time of meal preparation, or a fifth nutrient may be added upon request to customize a meal further, resource permitting. Nutrient chain may be listed in a sequentially ordered manner and mapped to the anticipated timescale for preparing a meal; timescale may be altered by applying different resource lists to different steps in nutrient chain and/or modifying nutrient chain by adding/subtracting branch points, removing/adding tasks, and the like. For instance and without limitation, a plurality of nutrient chain may be mapped to a 12-hr time scale for preparing a beef stew, wherein a negative time value represents "time out" from a meal being finished, and a positive time value represents "time post preparation," including for example delivery time, customer retrieval time, and the like. Nutrient chain may be optimized, combined, and or otherwise modified as described in further detail below to decrease average time of preparation.

Referring still to FIG. 1, apparatus 100 may generate a plurality of candidate nutrient chain combinations, wherein each nutrient chain combination may include a first nutrient chain of the plurality of nutrient chains and a second nutrient chain of the plurality of nutrient chains, and a first task of the first nutrient chain and a second task of the second nutrient chain are concurrently performed using a resource associated with each of the first task and the second task. A first task of a first nutrient chain and a second task of a second nutrient chain may be placed in a sequentially ordered sequence and/or performed concurrently relative to each other depending on constraints on task ordering and/or combination. For instance, a first task of a first nutrient chain may be to prepare a first meal at a station and a second task of a second nutrient chain may be to prepare a second meal, wherein the first meal introduces an allergen to be excluded from the second meal; this would introduce a constraint that would limit the sequential ordering in this manner. In such an example, the sequential order of the two different nutrient chains would need to be changed based on avoiding said allergen. In further non-limiting illustrative examples, a first task of a first nutrient chain may be to prepare 1 cup of a first nutrient and a second task of a second nutrient chain may be to prepare 1 cup of that same nutrient, a first task of a first nutrient chain and a second task of a second nutrient chain may be combined concurrently to improve efficiency, wherein a single person may prepare 2 cups at once. Determining if any constraint exists may include determining if a constraint would limit a first task of a first nutrient chain being ordered followed by a second task in a second nutrient chain in either a sequential and/or concurrent ordering. If either nutrient chain ordering is determined to be allowed based upon constraints, then ordering of a plurality of nutrient chains may be added to a feasible list for further feasibility quantifier analysis, as described in further detail below. In non-limiting illustrative examples, a plurality of nutrient chain may be concurrently listed, for instance combined into a plurality of candidate nutrient chain combinations determined by sequentially listing certain tasks and concurrently performing other tasks within a potential combination of nutrient chains, wherein concurrently performed tasks overlap at least for a moment in time, personnel, station, equipment, or overlap in any resource, as described above. In further non-limiting illustrative examples, concurrently performed tasks of two nutrient chains may involve, for instance and without limitation, a combination of resource at once such as preheating an oven of a first nutrient chain, washing utensils to remove allergens of a second nutrient chain, and chopping vegetables of a third nutrient chain. In such a non-limiting example, a first nutrient chain may correspond to preparing two distinct meals, such as a second meal and third meal, each of which may require heating in an oven at the same temperature, or at an average temperature suitable for both meals while using a single oven, wherein the average temperature is an optimized temperature calculated by a machine-learning model and/or objective function to batch cooking steps together, as described in further detail below; a second nutrient chain may correspond to removing allergens from a first meal that can be done while preparing a second meal and a third meal, but must be completed prior to finishing the preheating stage; a third nutrient chain may correspond to chopping vegetables that may correspond to an nutrient preparation task that overlaps with a plurality of meals.

Continuing in reference to FIG. 1, nutrient chain and candidate nutrient chain combinations may include signifiers, numerical values, alphanumerical codes, and the like that contain elements of data regarding identifiers related to certain combinations of nutrient chains elements, resource amounts, time amounts, constraints, and/or any other identifiable parameters that may be used in determining feasibility of an nutrient chain, or plurality of nutrient chain combinations, as described in further detail below. A machine-learning model may, for instance, retrieve nutrient chain from a meal database and determine feasibility of said nutrient chain by identification by a signifier, as described above.

Continuing in reference to FIG. 1, apparatus 100 may identify a plurality of constraints as a function of identifications of meals, which may include at least a resource constraint and at least a timing constraint. A "constraint," as used herein refers to a barrier, limitation, consideration, or any other constraint pertaining to resource utilization during optimizing the combination of a plurality of nutrient chains that may arise during meal preparation and/or delivery as a function of performing a plurality of nutrient chains combinations, wherein the constraint may alter the time and/or resources available to preparing a meal or performing a task, may alter the concurrent and/or sequential ordering of tasks in a plurality of nutrient chains, and/or may alter the feasibility of combining a plurality of nutrient chains. Constraints may be identified by an optimization process during optimization of nutrient chain combinations, as described in further detail below. A constraint may, for instance and without limitation, only appear during a particular optimized listing of a plurality of nutrient chain elements, wherein a second listing of the same elements in a different ordering may not show the same constraint. In non-limiting illustrative examples, a constraint may be a resource constraint, wherein dedicating an individual to a series of tasks for preparing a meal would then place a constraint on preparing a second meal with said individual, or performing a second combination of nutrient chains; likewise a constraint may be a time constraint wherein the maximal time allotted for selecting nutrient chains for an individual or set of individuals working in tandem in preparing a meal may be dictated by when a customer places an order, whether a customer is dine-in or take-out, delivery method for the meal, and/or type of meal and nutrients 116 used. Constraints may refer to customer preferences, for instance and without limitation, such as the presence of allergies, food intolerances, hypersensitivities, or other dietary constraints, philosophical, religious, and/or moral considerations to nutrients 116 and/or meal preparation, and the like; constraints may refer to seasonality of nutrients 116, nutrient amounts, nutrient substitutions, and/or other material and immaterial constraints to nutrient availability and use. Such information may be stored and/or retrieved by apparatus 100 from a database, for instance, via orders input by a restaurant wait staff, logged by a web based application, mobile application, or other meal ordering service, application, device, of the like. Meal orders may be provided in a non-electronic format and nutrient chain retrieved after a user prompts apparatus 100 for nutrient chain associated with an order, which may contain constraint information. Constraint information may be stored and/or retrieved alongside nutrient chain information by use of an alphanumeric code, numerical value, or any other method of signifying the presence, amount, and/or nature of a constraint related to a task, nutrient chain, and/or combinations of nutrient chain.

Continuing in reference to FIG. 1, apparatus 100 may be configured to generate plurality of candidate nutrient chain combinations by receiving feasibility training data. Feasibility training data may include a plurality of entries correlating task combinations with feasibility quantifiers. A "feasibility quantifier," as used in this disclosure is a score, metric, function, vector, matrix, numerical value, or the like, which describes a qualitative and/or quantitative mathematical proportion, propensity, or any relationship correlating the likelihood, possibility, and/or probability of completing a task, given a set of constraints and the a task's relationship in time to and ordering to other tasks, within a particular timeframe, wherein a timeframe may be determined by an identification of a meal, meal preparation time, expected delivery time, resource list, nutrient chain, and the like. Apparatus 100 may identify feasible combinations based on various constraints, wherein apparatus 100 may find and/or set values for those constraints or add a new constraint in the form of a "feasibility quantifier". In non-limiting illustrative examples, a feasibility quantifier may include scores relating the probability of feasibility for completing a series of tasks, wherein each task has an associated probability in relating preparation of a beef stew related to preparing the beef stew for a customer order within, for instance, a 15-minute time frame, 30-minute time frame, 1-hour time frame, etc. In further non-limiting illustrative examples, nutrient chain steps that would require more than a 15-minute time frame would garner scores indicating lower levels of feasibility, such as for instance placing beef in a marinade, chopping vegetables, and cooking a beef stock, and thus may result in candidate nutrient chain steps that would sequentially order meal preparation of such steps for a suitable amount of time prior to the 15-minute time frame. Additionally, in non-limiting illustrative examples, nutrient chain steps that could be completed within the 15-minute time frame of ordering may include combining the nutrients 116, and plating the meal, which would garner higher feasibility scores resulting in nutrient chain elements that may be combined in such a way that allows an individual to complete the entire nutrient chain combination to fulfill orders within 15 minutes of the customer placing the order. Feasibility quantifiers may be stored and/or retrieved from a database. Alternatively or additionally, determining the feasibility of an nutrient chain may include resource constraint information, as described in further detail below, wherein the feasibility of an individual completing a first candidate nutrient chain combination depends upon if that same individual is dedicated to a second candidate nutrient chain combination, and if the suitable kitchenware, utensils, appliances, workstations, and the like, are in use and/or if preparation of the next meal may result in an biological and/or philosophical conflict for a customer, for instance an allergy to peanuts, a lactose-free meal after cooking with milk, Kosher preparation, or a vegan meal. Feasibility quantifiers may incorporate information, for instance, if there would be enough time to prepare a second meal after a first meal, if a second meal would demand decontamination of a common space to avoid antigen cross-contamination. In such a non-limiting illustrative example, a feasibility quantifier may rank a candidate nutrient chain combination in such a way that gave a more favorable score to preparing a second meal first, followed by a first meal, as described in further detail below.

With continued reference to FIG. 1, apparatus 100 may be configured to generate a recipe machine-learning model. A "recipe machine-learning model," as used in this disclosure, is a mathematical representation of a relationship between inputs and outputs, as generated using any machine-learning process and/or machine-learning algorithm including without limitation any process as described herein, and stored in memory; an input is submitted to a machine-learning model once created, which generates an output based on the relationship that was derived. Generating recipe machine-learning model may include calculating one or more supervised machine-learning algorithms including active learning, classification, regression, analytical learning, artificial neural network, backpropagation, boosting, Bayesian statistics, case-based learning, genetic programming, Kernel estimators, naïve Bayes classifiers, maximum entropy classifier, conditional random field, K-nearest neighbor algorithm, support vector machine, random forest, ordinal classification, data pre-processing, statistical relational learning, and the like. Generating recipe machine-learning model may include calculating one or more unsupervised machine-learning algorithms, including a clustering algorithm such as hierarchical clustering, k-means clustering, mixture models, density based spatial clustering of algorithms with noise (DBSCAN), ordering points to identify the clustering structure (OPTICS), anomaly detection such as local outlier factor, neural networks such as autoencoders, deep belief nets, Hebbian learning, generative adversarial networks, self-organizing map, and the like. Generating recipe machine-learning model may include calculating a semi-supervised machine-learning algorithm such as reinforcement learning, self-learning, feature learning, sparse dictionary learning, anomaly detection, robot learning, association rules and the like. Recipe machine-learning model is trained by apparatus 100 using training data, including any of the training data as described herein. Training data may be obtained from records of previous iterations of generating recipe machine-learning model, user inputs and/or questionnaire responses, expert inputs, and the like. Recipe machine-learning model may be implemented as any machine-learning process, including for instance, and without limitation, as described in U.S. Nonprovisional application Ser. No. 16/375,303, filed on Apr. 4, 2019, and entitled "SYSTEMS AND METHODS FOR GENERATING ALIMENTARY INSTRUCTION SETS BASED ON VIBRANT CONSTITUTIONAL GUIDANCE," the entirety of which is incorporated herein by reference. Recipe machine-learning model is trained using training data to select recommended refreshments favored by a user selection. In an embodiment, user selection contained within a selection database may be utilized as training data to customize and train recipe machine-learning model individually for each user. For instance and without limitation, user selection that indicate a user prefers to eat foods that contain protein choices that contain either chicken, tofu or salmon and the user dislikes protein choices that contain beef or pork may be utilized as training data to generate recommended refreshments such as chicken picada, tofu and green bean stir fry, and miso glazed salmon, and to not generate recommended refreshments such as a ground beef stir fry or a pork burger. In another embodiment, recipe machine-learning model may output a plurality of recommended refreshments as a function of the health condition of the user. For instance and without limitation, a user may have a gluten allergy. In this example, recipe machine-learning model may output recommended refreshment suitable for the user where the recommended refreshment are gluten-free.

Figure 2:
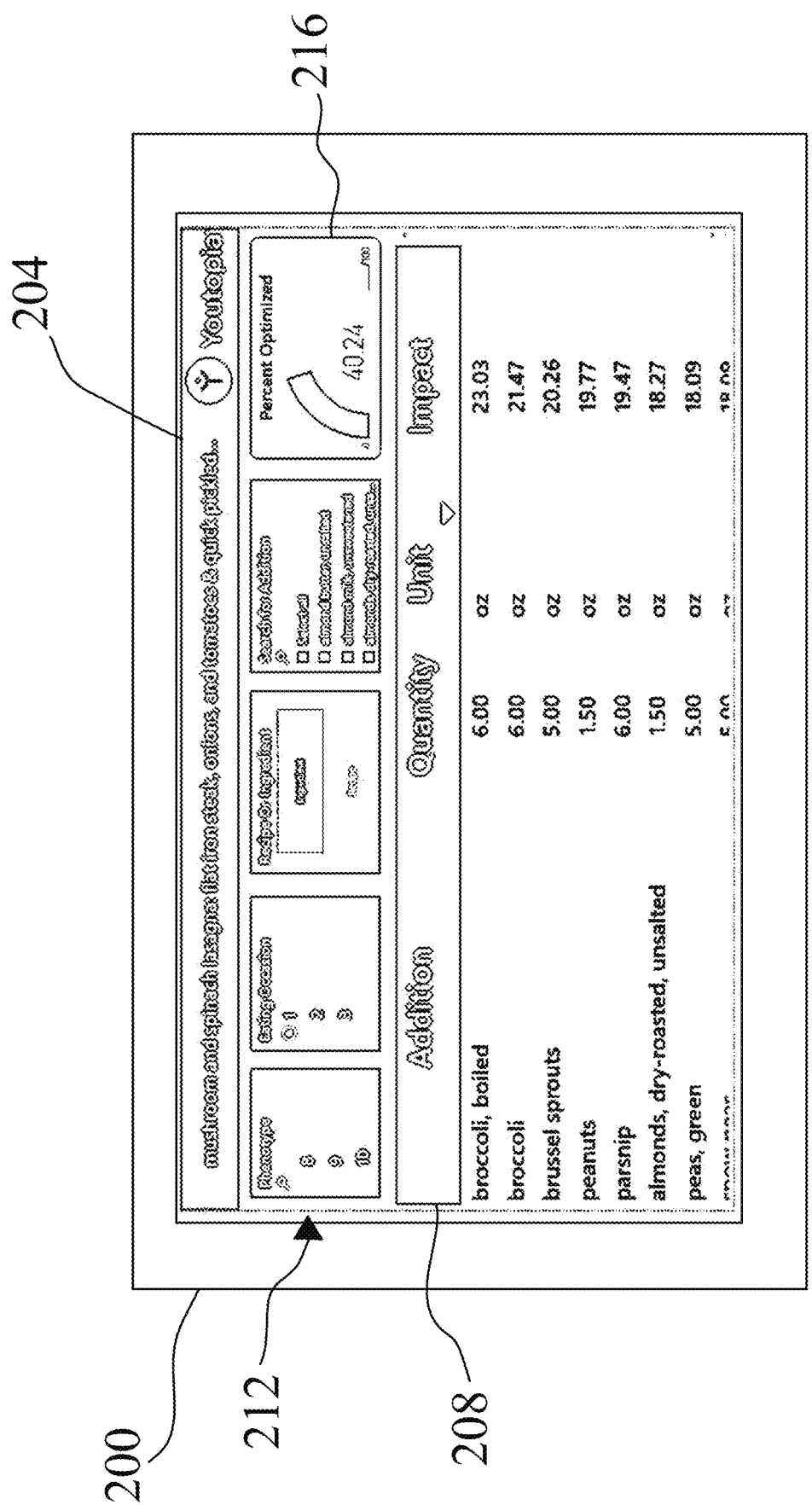
FIG. 2 illustrates an exemplary embodiment of a GUI.

Referring now to FIG. 2, an exemplary embodiment of a GUI 200 is presented. GUI 200 may include GUI 128 as described above with reference to FIG. 1. In some embodiments, GUI 200 may be displayed through, but not limited to, smartphones, tablets, laptops, monitors, and/or other display devices. GUI 200 may include meal title 204. A "meal title" as used in this disclosure is a name of a meal. Meal title 204 may be displayed at a top, bottom, and/or side portion of GUI 200. In some embodiments, meal title 204 may display a name of one or more meals. GUI 200 may display nutrient listing 208. An "nutrient listing" as used in this disclosure is a data set of one or more edible items. Nutrient listing 208 may include one or more base nutrients 116 of a recipe, additional nutrients 116 of a recipe, alternative nutrients 116 of a recipe, and the like, without limitation. In some embodiments, nutrient listing 208 may be displayed in a square grid having one or more columns and/or one or more rows. Nutrient listing 208 may include a listing of additional nutrients 116, base nutrients 116, quantity of nutrients 116, unit of measurement of nutrients 116, and/or an impact score of an nutrient. In some embodiments, GUI 200 may display one or more recommended and/or additional nutrients 116 through nutrient listing 208. Recommended and/or additional nutrients 116 may be calculated by apparatus 100 as a function of user data, edible data 108, and/or impact factors 120. In some embodiments, GUI 200 may include meal factors 212. A "meal factor" as used in this disclosure is one or more parameters of making a meal. Meal factors may include, but are not limited to, phenotypes, eating occasions, recipes and/or nutrients 116, additional nutrients 116, and/or optimization meter 216. An "eating occasion" as used in this disclosure is a temporal element of a meal. A temporal element of a meal may include, without limitation, a first meal, second meal, third meal, snack, breakfast, lunch, dinner, and the like. GUI 200 may display an indicator of a current eating occasion out of a plurality of eating occasions. GUI 200 may display one or more phenotypes that a meal of meal title 204 may be compatible with. For instance, and without limitation, GUI 200 may display meal factors 212 which may include a profile cluster 112 of phenotype 8, phenotype 9, and/or phenotype 10, which may be biologically compatible with a meal of meal title 204, such as mushroom and spinach lasagna, flat iron steak, onions, and tomatoes.

Still referring to FIG. 2, in some embodiments, GUI 200 may display one or more levels of optimization meter 216. An "optimization meter" as used in this discourse is a graphical element showing a portion of a maximum value. Optimization meter 216 may display one or more numbers, values, gauges, and the like, without limitation. Optimization meter 216 may be generated by apparatus 100 as a function of user data and/or impact factors 120. For instance and without limitation, optimization meter 216 may display a gauge in a shape of a half circle being 40.24% full, which may indicate a current meal represented in meal title 204 is 40.24% optimized. Optimization meter 216 may display one or more colors which may represent one or more levels of optimization. For instance, and without limitation, optimization meter 216 may display a red color of a gauge indicating a low optimization percentage, such as 40.24%. Apparatus 100 may determine an optimization percentage through comparing one or more phenotypes with one or more nutrients 116, impact factors, user goals, and the like.

Figure 3:
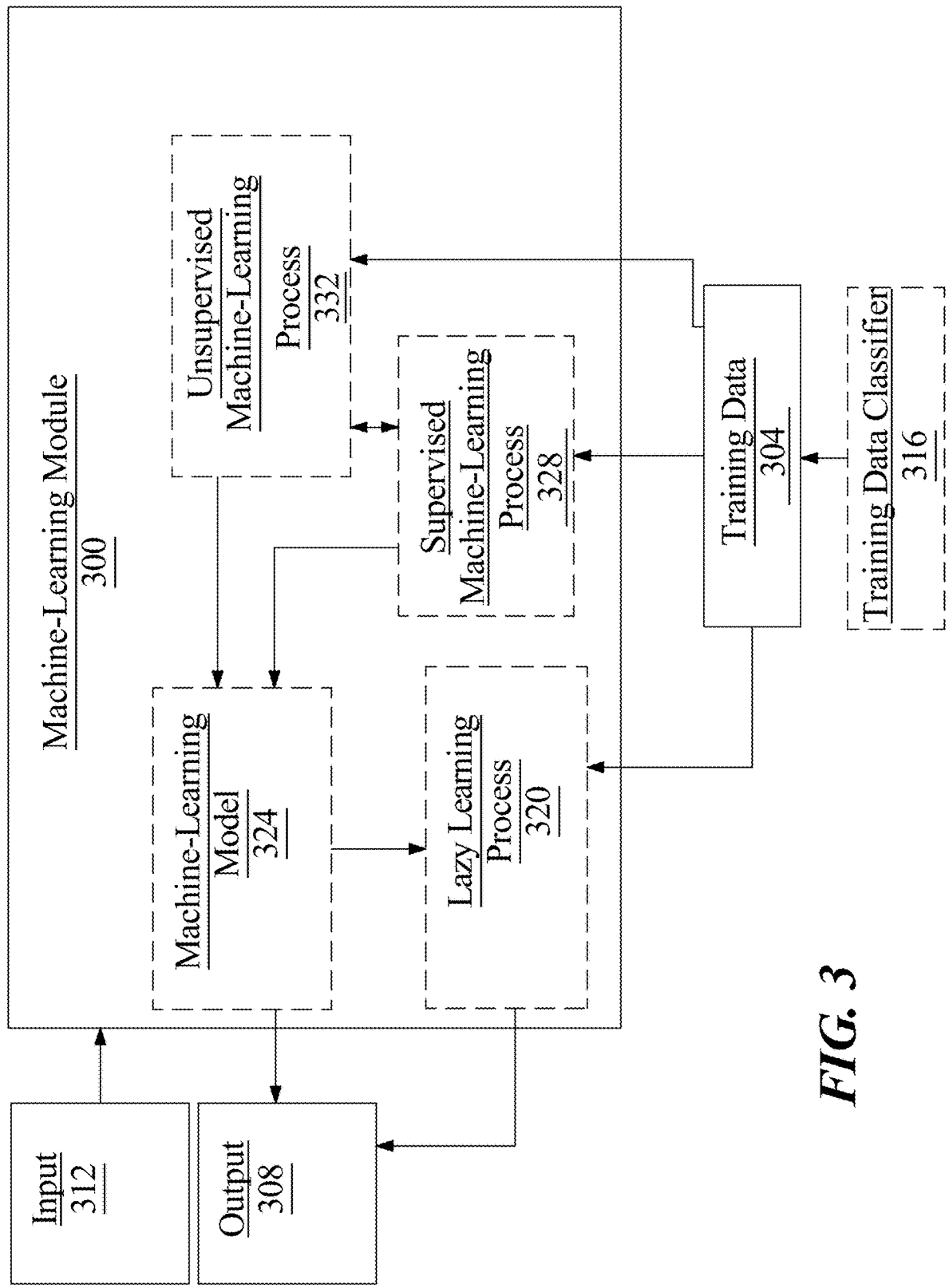
FIG. 3 is an exemplary embodiment of a machine learning model.

Referring now to FIG. 3, an exemplary embodiment of a machine-learning module 300 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 304 to generate an algorithm that will be performed by a computing device/module to produce outputs 308 given data provided as inputs 312; this is in contrast to a non-machine learning software program where the commands to be executed are determined in advance by a user and written in a programming language.

Still referring to FIG. 3, "training data," as used herein, is data containing correlations that a machine-learning process may use to model relationships between two or more categories of data elements. For instance, and without limitation, training data 304 may include a plurality of data entries, each entry representing a set of data elements that were recorded, received, and/or generated together; data elements may be correlated by shared existence in a given data entry, by proximity in a given data entry, or the like. Multiple data entries in training data 304 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 304 according to various correlations; correlations may indicate causative and/or predictive links between categories of data elements, which may be modeled as relationships such as mathematical relationships by machine-learning processes as described in further detail below. Training data 304 may be formatted and/or organized by categories of data elements, for instance by associating data elements with one or more descriptors corresponding to categories of data elements. As a non-limiting example, training data 304 may include data entered in standardized forms by persons or processes, such that entry of a given data element in a given field in a form may be mapped to one or more descriptors of categories. Elements in training data 304 may be linked to descriptors of categories by tags, tokens, or other data elements; for instance, and without limitation, training data 304 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 3, training data 304 may include one or more elements that are not categorized; that is, training data 304 may not be formatted or contain descriptors for some elements of data. Machine-learning algorithms and/or other processes may sort training data 304 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 304 to be made applicable for two or more distinct machine-learning algorithms as described in further detail below. Training data 304 used by machine-learning module 300 may correlate any input data as described in this disclosure to any output data as described in this disclosure. As a non-limiting illustrative example inputs may include recipe data and outputs may include impact factors.

Further referring to FIG. 3, training data may be filtered, sorted, and/or selected using one or more supervised and/or unsupervised machine-learning processes and/or models as described in further detail below; such models may include without limitation a training data classifier 316. Training data classifier 316 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 300 may generate a classifier using a classification algorithm, defined as a processes whereby a computing device and/or any module and/or component operating thereon derives a classifier from training data 304. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 316 may classify elements of training data to impact factors, macronutrients, micronutrients, and the like.

Still referring to FIG. 3, machine-learning module 300 may be configured to perform a lazy-learning process 320 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 304. Heuristic may include selecting some number of highest-ranking associations and/or training data 304 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 3, machine-learning processes as described in this disclosure may be used to generate machine-learning models 324. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 324 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 324 may be generated by creating an artificial neural network, such as a convolutional neural network comprising an input layer of nodes, one or more intermediate layers, and an output layer of nodes. Connections between nodes may be created via the process of "training" the network, in which elements from a training data 304 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 3, machine-learning algorithms may include at least a supervised machine-learning process 328. At least a supervised machine-learning process 328, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include recipe data as described above as inputs, impact factors as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 304. Persons skilled in the art, upon reviewing the entirety of this disclosure, will be aware of various possible variations of at least a supervised machine-learning process 328 that may be used to determine relation between inputs and outputs. Supervised machine-learning processes may include classification algorithms as defined above.

Further referring to FIG. 3, machine learning processes may include at least an unsupervised machine-learning processes 332. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 3, machine-learning module 300 may be designed and configured to create a machine-learning model 324 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 3, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Figure 4:
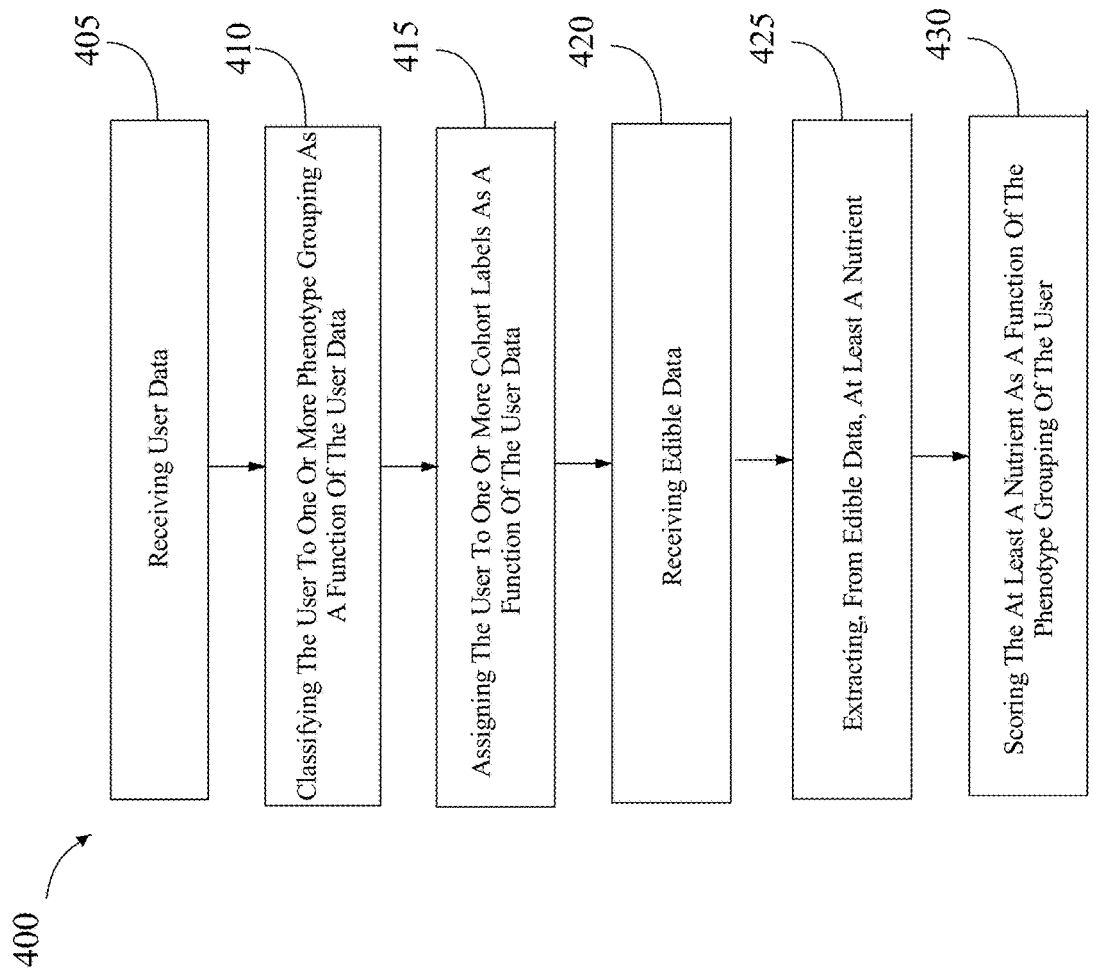
FIG. 4 is a flowchart of a method of generating a nutrient chain.

Referring now to FIG. 4, a method 400 of scoring a nutrient is presented. At step 405, method 400 includes receiving, at a computing device, user data from a user. This step may be implemented as described above with reference to FIGS. 1-3, without limitation.

Still referring to FIG. 4, at step 410, method 400 includes classifying, at a computing device, a user to a profile cluster as a function of user data. In some embodiments, classification may include using a classifier. In some embodiments, a computing device may be configured to determine a nutrient target range of one or more users. A computing device may display a nutrient target range of one or more users through a graphical user interface. This step may be implemented as described above with reference to FIGS. 1-3, without limitation.

Still referring to FIG. 4, at step 415, method 400 may include assigning, by the processor, the user one or more cohort labels as a function of the user data. In some embodiments, assigning the user one or more cohort labels further may include assigning at least a first cohort label associated with a first cluster and assigning a second cohort label associated with the at least a second cluster. This step may be implemented as described above with reference to FIGS. 1-3, without limitation.

Still referring to FIG. 4, at step 420, method 400 includes receiving, at a computing device, edible data. Receiving edible data may include generating a web search for edible data. This step may be implemented as described above with reference to FIGS. 1-3, without limitation.

Still referring to FIG. 4, at step 425, method 400 includes extracting, at a computing device, from edible data, at least a nutrient. Extraction may include using a language processing model. This step may be implemented as described above with reference to FIGS. 1-3, without limitation.

Still referring to FIG. 4, at step 430, method 400 includes scoring, at a computing device, at least a nutrient as a function of a profile cluster of a user. Scoring may include using an objective function. Scoring may include a plurality of nutrients of the at least a nutrient as a function of a plurality of profile clusters. Scoring may include scoring a plurality of nutrients of at least a nutrient of edible data based on impact factors. This step may be implemented as described above with reference to FIGS. 1-3, without limitation.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 5:
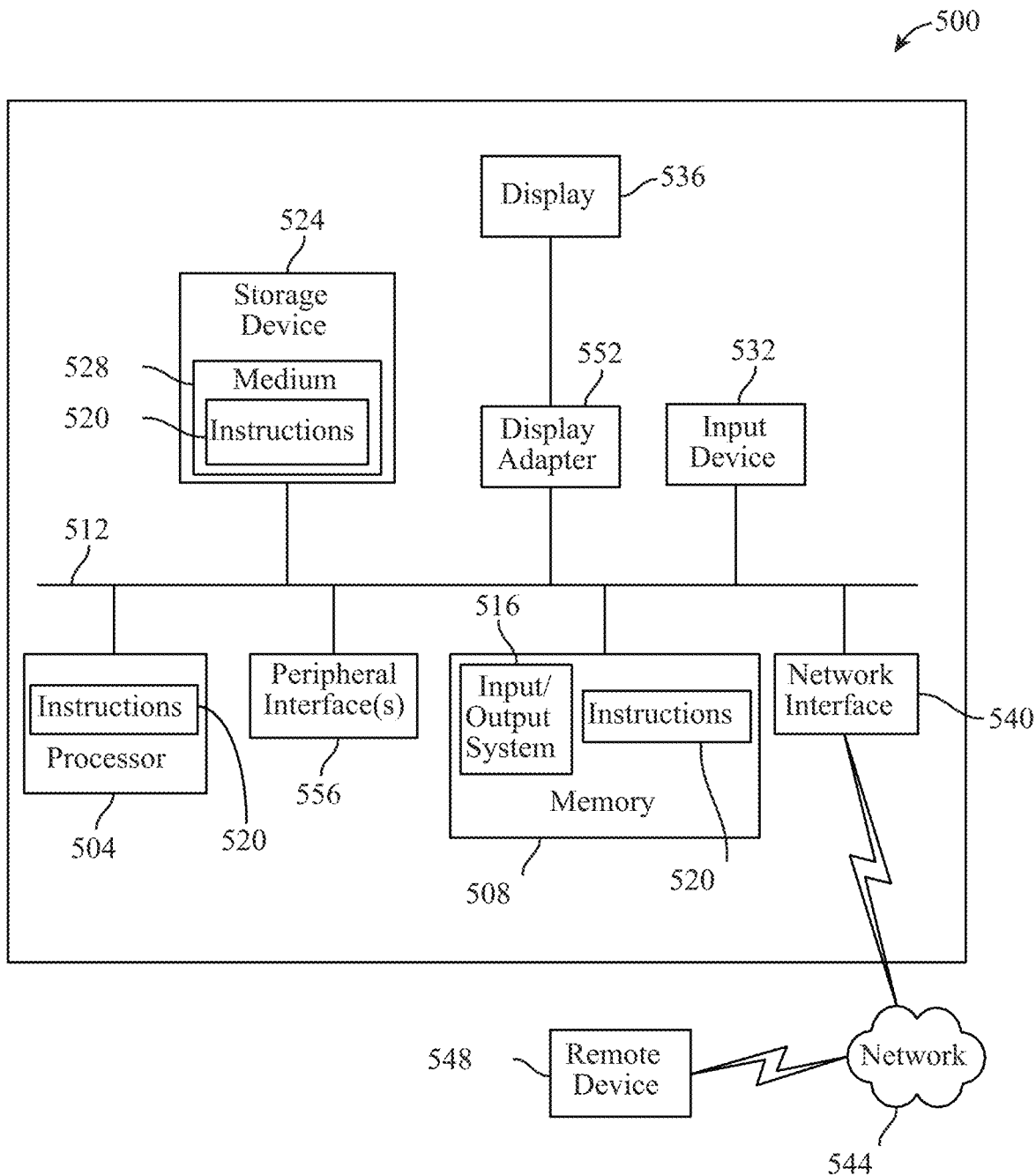
FIG. 5 is a block diagram of a computing system that can be used to implement any one or more of the methodologies disclosed herein and any one or more portions thereof.

FIG. 5 shows a diagrammatic representation of one embodiment of a computing device in the exemplary form of a computer system 500 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 500 includes a processor 504 and a memory 508 that communicate with each other, and with other components, via a bus 512. Bus 512 may include any of several types of bus structures including, but not limited to, a memory bus, a memory controller, a peripheral bus, a local bus, and any combinations thereof, using any of a variety of bus architectures.

Processor 504 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 504 may be organized according to Von Neumann and/or Harvard architecture as a non-limiting example. Processor 504 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 508 may include various components (e.g., machine-readable media) including, but not limited to, a random-access memory component, a read only component, and any combinations thereof. In one example, a basic input/output system 516 (BIOS), including basic routines that help to transfer information between elements within computer system 500, such as during start-up, may be stored in memory 508. Memory 508 may also include (e.g., stored on one or more machine-readable media) instructions (e.g., software) 520 embodying any one or more of the aspects and/or methodologies of the present disclosure. In another example, memory 508 may further include any number of program modules including, but not limited to, an operating system, one or more application programs, other program modules, program data, and any combinations thereof.

Computer system 500 may also include a storage device 524. Examples of a storage device (e.g., storage device 524) include, but are not limited to, a hard disk drive, a magnetic disk drive, an optical disc drive in combination with an optical medium, a solid-state memory device, and any combinations thereof. Storage device 524 may be connected to bus 512 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 524 (or one or more components thereof) may be removably interfaced with computer system 500 (e.g., via an external port connector (not shown)). Particularly, storage device 524 and an associated machine-readable medium 528 may provide nonvolatile and/or volatile storage of machine-readable instructions, data structures, program modules, and/or other data for computer system 500. In one example, software 520 may reside, completely or partially, within machine-readable medium 528. In another example, software 520 may reside, completely or partially, within processor 504.

Computer system 500 may also include an input device 532. In one example, a user of computer system 500 may enter commands and/or other information into computer system 500 via input device 532. Examples of an input device 532 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 532 may be interfaced to bus 512 via any of a variety of interfaces (not shown) including, but not limited to, a serial interface, a parallel interface, a game port, a USB interface, a FIREWIRE interface, a direct interface to bus 512, and any combinations thereof. Input device 532 may include a touch screen interface that may be a part of or separate from display 536, discussed further below. Input device 532 may be utilized as a user selection device for selecting one or more graphical representations in a graphical interface as described above.

A user may also input commands and/or other information to computer system 500 via storage device 524 (e.g., a removable disk drive, a flash drive, etc.) and/or network interface device 540. A network interface device, such as network interface device 540, may be utilized for connecting computer system 500 to one or more of a variety of networks, such as network 544, and one or more remote devices 548 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 544, may employ a wired and/or a wireless mode of communication. In general, any network topology may be used. Information (e.g., data, software 520, etc.) may be communicated to and/or from computer system 500 via network interface device 540.

Computer system 500 may further include a video display adapter 552 for communicating a displayable image to a display device, such as display device 536. Examples of a display device include, but are not limited to, a liquid crystal display (LCD), a cathode ray tube (CRT), a plasma display, a light emitting diode (LED) display, and any combinations thereof. Display adapter 552 and display device 536 may be utilized in combination with processor 504 to provide graphical representations of aspects of the present disclosure. In addition to a display device, computer system 500 may include one or more other peripheral output devices including, but not limited to, an audio speaker, a printer, and any combinations thereof. Such peripheral output devices may be connected to bus 512 via a peripheral interface 556. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for scoring a nutrient, comprising:
   at least a processor; and
   a memory communicatively connected to the at least a processor, the memory containing instructions configuring the at least a processor to:
      receive user data and edible data;
      extract, from the edible data, a plurality of nutrients, wherein extracting the plurality of nutrients comprises performing a web search configured to generate a plurality of weights to a plurality of semantic elements of the edible data, wherein extracting the plurality of nutrients further comprises using at least an optical character recognition (OCR) process by converting the edible data into machine-encoded text by the at least an OCR process, wherein converting the edible data into the machine-encoded text comprises converting images of text in the edible data into the machine-encoded text and further comprises:
         pre-processing image components of the images, wherein pre-processing the image components comprises:
            de-skewing at least one of the image components by applying a homography transform to the at least one of the image components;
            converting at least a portion of one of the images from color or greyscale to a binary image format; and
            normalizing an aspect ratio of at least one of the image components;
         implementing an OCR algorithm comprising a matrix matching process, wherein implementing the OCR algorithm comprises:
            comparing pixels of at least one of the pre-processed images to pixels of a stored glyph on a pixel-by-pixel basis; and
            ascertaining a similar font and scale therebetween based on the comparison; and
         post-processing an output of the matrix matching process to increase OCR accuracy by constraining the output to a lexicon containing a set of words whose occurrence is permitted;
      classify the plurality of nutrients, extracted from the edible data using the at least an OCR process, to a plurality of impact factors utilizing a nutrient classifier, wherein the nutrient classifier is configured to receive a meal ID and recipe data as an input and output the plurality of impact factors matched to a plurality of nutrition data elements of the meal ID and the recipe data;
      classify a user to a profile cluster as a function of at least an element of the user data, wherein the profile cluster comprises a grouping of phenotypes;
      assign the user one or more cohort labels as a function of the profile cluster;
      score at least a nutrient of the plurality of nutrients as a function of the cohort label and the plurality of impact factors, wherein scoring the at least a nutrient comprises:
         generating training data correlating phenotype data to nutrient scores, wherein the nutrient scores comprise the plurality of weights derived by the web search;
         iteratively training a nutrient score machine learning model using the training data, wherein iteratively training the nutrient score machine learning model further comprises:
            using training data applied to an input layer of nodes comprising at least one input node, one or more intermediate layers of nodes, and an output layer of nodes;
            adjusting one or more connections and one or more weights between nodes in adjacent layers of the machine learning model;
            detecting additional correlations between the output layer of nodes and the input layer of nodes;
            identifying a plurality of nutrients as a function of edible data;
            updating the training data based on user input comprising additional training data;
            retraining the nutrient score machine learning model using the detected additional correlations between the output layer of nodes and the input layer of nodes; and
         generating, as a function of the nutrient score machine learning model, a nutrient score; and
      generate a nutrient chain by comparing one or more impact factors of the plurality of impact factors with the at least a nutrient of the plurality of nutrients using an objective function, wherein:
         the objective function comprises an optimization criterion; and
         the optimization criterion assigns weights to each of the one or more impact factors, wherein the one or more impact factors are a metric of influence of one or more nutrients on an individual's biological system.

2. The apparatus of claim 1, wherein the memory contains instructions further configuring the at least a processor to score the at least a nutrient based on the one or more impact factors.

3. The apparatus of claim 1, wherein the memory contains instructions configuring the at least a processor to generate a plurality of nutrient chain combinations.

4. The apparatus of claim 1, wherein scoring the at least a nutrient further comprises utilizing at least one objective function to score the at least a nutrient.

5. The apparatus of claim 1, wherein assigning the user one or more cohort labels further comprises assigning at least a first cohort label associated with a first cluster and assigning a second cohort label associated with at least a second cluster.

6. The apparatus of claim 1, wherein the at least a processor is further configured to:
   receive additional user data;
   reclassify the user to additional groupings of phenotypes as a function of the additional user data; and
   assign the user one or more additional cohort labels as a function of the additional user data.

7. The apparatus of claim 6, wherein the at least a processor is further configured to score the at least a nutrient as a function of the one or more additional cohort labels.

8. The apparatus of claim 1, wherein the memory contains instructions further configuring the at least a processor to determine a nutrition target range.

9. The apparatus of claim 1, wherein the memory contains instructions further configuring the at least a processor to display, through a graphical user interface, the score of the at least a nutrient.

10. A method of scoring a nutrient using a computing device, comprising:
   receiving, using at least a processor, user data from a user;
   classifying, by the at least a processor, the user to a profile cluster as a function of the user data, wherein the profile cluster comprises a grouping of phenotypes;
   assigning, by the at least a processor, the user one or more cohort labels as a function of the user data;
   receiving, by the at least a processor, edible data;
   extracting, by the at least a processor, from the edible data, a plurality of nutrients, wherein extracting the plurality of nutrients comprises performing a web search configured to generate a plurality of weights to a plurality of semantic elements of the edible data, wherein extracting the plurality of nutrients further comprises using at least an optical character recognition (OCR) process by converting the edible data into machine-encoded text by the at least an OCR process, wherein converting the edible data into the machine-encoded text comprises converting images of text in the edible data into the machine-encoded text and further comprises:
      pre-processing image components of the images, wherein pre-processing the image components comprises:
         de-skewing at least one of the image components by applying a homography transform to the at least one of the image components;
         converting at least a portion of one of the images from color or greyscale to a binary image format; and
         normalizing an aspect ratio of at least one of the image components;
      implementing an OCR algorithm comprising a matrix matching process, wherein implementing the OCR algorithm comprises:
         comparing pixels of at least one of the pre-processed images to pixels of a stored glyph on a pixel-by-pixel basis; and
         ascertaining a similar font and scale therebetween based on the comparison; and
      post-processing an output of the matrix matching process to increase OCR accuracy by constraining the output to a lexicon containing a set of words whose occurrence is permitted;
   classifying, by the at least a processor, the plurality of nutrients, extracted from the edible data using the at least an OCR process, to a plurality of impact factors utilizing a nutrient classifier, wherein the nutrient classifier is configured to receive a meal ID and recipe data as an input and output the plurality of impact factors matched to a plurality of nutrition data elements of the meal ID and the recipe data;
   scoring, by the at least a processor, at least a nutrient of the plurality of nutrients as a function of the profile cluster of the user and the plurality of impact factors, wherein scoring the at least a nutrient comprises:
      generating training data correlating phenotype data to nutrient scores, wherein the nutrient scores comprise the plurality of weights derived by the web search;
      iteratively training a nutrient score machine learning model using the training data, wherein iteratively training the nutrient score machine learning model comprises:
         updating the training data based on user input comprising additional training data;
         using training data applied to an input layer of nodes comprising at least one input node, one or more intermediate layers of nodes, and an output layer of nodes;
         adjusting one or more connections and one or more weights between nodes in adjacent layers of the machine learning model;
         detecting additional correlations between the output layer of nodes and the input layer of nodes;
         identifying a plurality of nutrients as a function of edible data; and
      generating, as a function of the nutrient score machine learning model, a nutrient score; and
   generating, by the at least a processor, a nutrient chain by comparing one or more impact factors of the plurality of impact factors with the at least a nutrient of the plurality of nutrients using an objective function, wherein:
      the objective function comprises an optimization criterion; and
      the optimization criterion assigns weights to each of the one or more impact factors, wherein the one or more impact factors are a metric of influence of one or more nutrients on an individual's biological system.

11. The method of claim 10, wherein scoring the at least a nutrient further comprises scoring, by the at least a processor, the at least a nutrient of the edible data based on the one or more impact factors.

12. The method of claim 10, further comprising generating, by the at least a processor, a plurality of nutrient combinations.

13. The method of claim 10, wherein scoring the at least a nutrient further comprises utilizing at least one objective function to generate the score of the at least a nutrient.

14. The method of claim 10, wherein assigning the user one or more cohort labels further comprises assigning at least a first cohort label associated with a first cluster and assigning a second cohort label associated with at least a second cluster.

15. The method of claim 10, further comprising:
receiving, by the at least a processor, additional user data;
reclassifying, by the at least a processor, the user to additional groupings of phenotypes as a function of the additional user data; and
assigning, by the at least a processor, the user one or more additional cohort labels as a function of the additional user data.

16. The method of claim 15, wherein scoring the at least a nutrient comprises scoring the at least a nutrient as a function of the one or more additional cohort labels.

17. The method of claim 10, further comprising determining, by the at least a processor, a nutrition target range.

18. The method of claim 10, further comprising displaying, through a graphical user interface, the score of the at least a nutrient.

* * * * *